US011602585B2

(12) United States Patent
Chan et al.

(10) Patent No.: US 11,602,585 B2
(45) **Date of Patent: *Mar. 14, 2023**

(54) METHODS FOR REDUCING CONTAMINATION IN A BIOLOGICAL SUBSTANCE

(71) Applicant: CytoSorbents Corporation, Monmouth Junction, NJ (US)

(72) Inventors: Phillip P. Chan, Cherry Hill, NJ (US); Vincent J. Capponi, Monmouth Junction, NJ (US); Thomas D. Golobish, Princeton, NJ (US); Humayra Begum Ali, Princeton, NJ (US)

(73) Assignee: CytoSorbents Corporation, Monmouth Junction, NJ (US)

( * ) Notice: Subject to any disclaimer, the term of this patent is extended or adjusted under 35 U.S.C. 154(b) by 340 days.

This patent is subject to a terminal disclaimer.

(21) Appl. No.: 15/497,640

(22) Filed: Apr. 26, 2017

(65) Prior Publication Data

US 2017/0224903 A1 Aug. 10, 2017

Related U.S. Application Data

(63) Continuation of application No. 14/410,901, filed as application No. PCT/US2013/048615 on Jun. 28, 2013.

(60) Provisional application No. 61/666,626, filed on Jun. 29, 2012.

(51) Int. Cl.

| | |
|---|---|
| ***A61M 1/36*** | (2006.01) |
| ***A61K 9/16*** | (2006.01) |
| ***B01J 20/28*** | (2006.01) |
| ***A61K 31/765*** | (2006.01) |
| ***B01J 20/26*** | (2006.01) |
| ***C08F 299/00*** | (2006.01) |
| ***C08J 9/26*** | (2006.01) |

(52) U.S. Cl.

CPC ............ *A61M 1/3679* (2013.01); *A61K 9/16* (2013.01); *A61K 31/765* (2013.01); *B01J 20/261* (2013.01); *B01J 20/28069* (2013.01); *B01J 20/28078* (2013.01); *C08F 299/00* (2013.01); *C08J 9/26* (2013.01); *A61M 2202/0057* (2013.01); *A61M 2202/0405* (2013.01); *A61M 2202/049* (2013.01); *A61M 2202/0413* (2013.01); *A61M 2202/0415* (2013.01); *A61M 2202/0423* (2013.01); *A61M 2202/0464* (2013.01); *A61M 2202/0466* (2013.01); *A61M 2202/0492* (2013.01); *A61M 2202/0496* (2013.01); *A61M 2202/20* (2013.01); *A61M 2202/203* (2013.01); *A61M 2202/206* (2013.01); *C08J 2201/0444* (2013.01); *C08J 2207/10* (2013.01); *C08J 2353/00* (2013.01)

(58) Field of Classification Search

None

See application file for complete search history.

(56) References Cited

U.S. PATENT DOCUMENTS

| | | | | |
|---|---|---|---|---|
| 5,633,290 | A * | 5/1997 | Frechet | B01D 67/0093 502/402 |
| 5,726,118 | A | 3/1998 | Ivey et al. | |
| 6,890,523 | B2 | 5/2005 | Bacon Kurtz et al. | |
| 7,678,369 | B2 | 3/2010 | Bacon Kurtz et al. | |
| 2003/0027879 | A1 | 2/2003 | Davankov et al. | |
| 2006/0099169 | A1 | 5/2006 | Charmot et al. | |
| 2008/0119576 | A1 | 5/2008 | Young et al. | |
| 2008/0213523 | A1 | 9/2008 | Fujimoto et al. | |
| 2010/0172861 | A1 | 7/2010 | Bacon Kurtz et al. | |
| 2011/0070424 | A1 | 3/2011 | Young et al. | |
| 2013/0011824 | A1 | 1/2013 | Chan et al. | |

FOREIGN PATENT DOCUMENTS

| | | |
|---|---|---|
| CN | 101307149 B | 6/2011 |
| JP | 2002-035118 A | 2/2002 |
| WO | WO0043120 | 7/2000 |
| WO | WO2005123952 | 12/2005 |
| WO | WO2006086428 | 8/2006 |
| WO | WO2009158027 | 12/2009 |

(Continued)

OTHER PUBLICATIONS

McFarland, "Emerging therapies for Clostridium difficile infections", Expert Opinion on Emerging Drugs, 16:3, 2011, pp. 425-439. (Year: 2011).*

(Continued)

*Primary Examiner* — Melissa L Fisher

(74) *Attorney, Agent, or Firm* — BakerHostetler

(57) ABSTRACT

Provided herein are materials and methods of reducing contamination in a biological substance or treating contamination in a subject by one or more toxins comprising contacting the biological substance with an effective amount of a sorbent capable of sorbing the toxin, wherein the sorbent comprises a plurality of pores ranging from 50 Å to 40,000 Å with a pore volume of 0.5 cc/g to 5.0 cc/g and a size of 0.05 mm to 2 cm and sorbing the toxin. Also provided are kits to reduce contamination by one or more toxins in a biological substance comprising a sorbent capable of sorbing a toxin, wherein the sorbent comprises a plurality of pores ranging from 50 Å to 40,000 Å with a pore volume of 0.5 cc/g to 5.0 cc/g and a size of 0.05 mm to 2 cm and a vessel to store said sorbent when not in use together with packaging for same.

25 Claims, 3 Drawing Sheets

(56) References Cited

FOREIGN PATENT DOCUMENTS

| | | | |
|---|---|---|---|
| WO | WO2011070363 | | 6/2011 |
| WO | 2011100354 | A1 | 8/2011 |
| WO | WO2011123767 | | 10/2011 |
| WO | WO 2012/033522 | A1 | 3/2012 |
| WO | WO2012094565 | | 7/2012 |
| WO | WO2013025483 | | 2/2013 |
| WO | WO 2014/005039 | A2 | 1/2014 |

OTHER PUBLICATIONS

Taniguchi et al. "Novel adsorbent of circulating bacterial toxins and cytokines: The effect of direct hemoperfusion with CTR column for the treatment of experimental endotoxemia", Grit Care Med, 34(3), 2006, pp. 800-806.

Anderson et al., "The Human Plasma Proteome History, Character, and Diagnostic Prospects", Molecular & Cellular Proteomics, American Society for Biochemistry and Molecular Biology, Jan. 1, 2002, 845-867.

"CytoSorb is a Novel Application of Tried and True Technology", Chemistfrog's Instablog, Seeking Alpha, Chemistfrog 11, http://seekinqalgha.com/instablog/399559- chemistfrog/78833-cytosorb-is-a-novel-application-of-tried-and-true-technology, Jun. 28, 2010, 2 pages.

Banno et al., "Biochemical Characterization and Biologic Actions of Two Toxins (D-1 and D-2) from Clostridium Difficile", Clinical Infectious Disease, 1984, 6 (Supp. 1), S11-S20.

Banno et al., "Two Toxins (D-1 and D-2) of Clostridium Difficile Causing Antibiotic- Associated Colitis: Purification and Some Characterization", Biochem. Int., 1981, 2(6), 629-635.

Gerding et al., "Treatment of Clostridium Difficile Infection", Clinical Infectious Diseases, 2008, 46(Supp 1), S32-S42.

Gill et al., "Foodborne Illnesses", Current Treatment Options In Gastroenterology, 2001, 4, 23-38.

Gouliouris et al., "Prevention and Treatment of Clostridium Difficile Infection", Clinical Medicine, 2011, 11(1), 75-79.

Johal et al., "Differential Effects of Varying Concentrations of Clostridium difficile Toxin A on Epithelial Barrier Function and Expression of Cytokines", The Journal of Infectious Disease, 2004, 189, 2110-2119.

Kopic et al., "Toxin Mediated Diarrhea in the 21st Century: The Pathophysiology of Intestinal Ion Transport in the Course of ETEC, V. Cholerae and Rotavirus Infection", Toxins, 2010, 2, 2132-2157.

Krivan et al., "Purification of Clostridium Difficile Toxin A by Affinity Chromatography on Immobilized Thyroglobulin", Infection and Immunity, 1987, 55(8), 1873-1877.

Lyerly et al., "Characterization of Toxins A and B of Clostridium Difficile with Monoclonal Antibodies", Infection and Immunity, 1986, 70-76.

Lyerly et al., "Clostridium Difficile: Its Disease and Toxins", Clinical Microbiology Reviews, 1988, 1-18.

Wagner, Jr., "Baterial Food Poisoning", Texas Agricultural Extension Service, www.ecosafeusa.com, 1989, 6 pages.

Modern Physician, vol. 31, No. 5, 2011, pp. 574-577 [Cited in JP OA on Oct. 17, 2017].

Office Action issued in Japanese Patent Application No. 2015-520580, dated Oct. 17, 2017.

European Patent Application No. 20158282.2; Extended Search Report; dated May 11, 2020; 11 pages.

* cited by examiner

METHODS FOR REDUCING CONTAMINATION IN A BIOLOGICAL SUBSTANCE

CROSS-REFERENCE TO RELATED APPLICATION

This application is a continuation of U.S. patent application Ser. No. 14/410,901, filed Dec. 23, 2014, and claims the benefit of PCT Patent Application No. PCT/US2013/048615, filed Jun. 28, 2013 and U.S. Provisional Application No. 61/666,626, filed Jun. 29, 2012, each of which is incorporated herein by reference in its entirety.

TECHNICAL FIELD

The present invention relates generally to materials, methods, kits and devices for the reduction of toxin contamination.

BACKGROUND

Toxins are exogenous or endogenous substances that cause a disruption in normal physiologic functions and may cause disease. They cause disease by coming in contact with or being absorbed by body tissues that include the intestines, skin or mucosal membranes. There are thousands, if not millions of substances that can act as toxins. Even some substances that are normally not toxins can become toxins under the proper conditions. Toxins vary significantly in their strength and the rapidity in which they act. Treatments have been developed for exposure to toxins and include removal from contact with the toxin, and the use of antidotes.

Antidotes are substances that can counter act the effects of toxins. However, most antidotes are specific to only one type of toxin or family of toxins. Therefore, it is impossible for hospitals, clinics, field hospitals, doctor's offices, ambulances, and other first responders to carry an antidote for every toxin. In addition, antidotes have not been developed for many toxins and quantities of some antidotes may be too distant to effectively be used in the treatment of some exposures to toxins.

Thus, there is a need for new and better materials, methods, kits and devices for the quick, effective and efficient reduction of toxin contamination and treatment of toxin contamination in a subject.

SUMMARY

Provided herein are suitable materials and methods of reducing contamination by one or more toxins in a biological substance comprising contacting the biological substance with an effective amount of a sorbent capable of sorbing the toxin, wherein the sorbent comprises a plurality of pores ranging from 50 Å to 40,000 Å with a pore volume of 0.5 cc/g to 5.0 cc/g and a size of 0.05 mm to 2 cm and sorbing the toxin. Also provided herein are suitable methods of treating contamination by one or more toxins in a subject in need thereof comprising contacting a biological substance of the subject with an effective amount of a sorbent capable of sorbing the toxin, wherein the sorbent comprises a plurality of pores ranging from 50 Å to 40,000 Å with a pore volume of 0.5 cc/g to 5.0 cc/g and a size of 0.05 mm to 2 cm and sorbing the toxin.

Provided herein are also suitable kits to reduce contamination by one or more toxins in a biological substance comprising a sorbent capable of sorbing a toxin, wherein the sorbent comprises a plurality of pores ranging from 50 Å to 40,000 Å with a pore volume of 0.5 cc/g to 5.0 cc/g and a size of 0.05 mm to 2 cm and a vessel to store said sorbent when not in use together with packaging for same. Also provided herein are suitable devices to reduce contamination by one or more toxins in a biological substance comprising a sorbent capable of sorbing a toxin, wherein the sorbent comprises a plurality of pores ranging from 50 Å to 40,000 Å with a pore volume of 0.5 cc/g to 5.0 cc/g and a size of 0.05 mm to 2 cm and a vessel wherein the sorbent is located inside the vessel such that the biological substance can be directly introduced into the vessel.

Also provided herein are suitable pharmaceutical compositions comprising a sorbent capable of sorbing a toxin, wherein the sorbent comprises a plurality of pores ranging from 50 Å to 40,000 Å with a pore volume of 0.5 cc/g to 5.0 cc/g and a size of 0.05 mm to 2 cm and a food product or a potable liquid.

Provided herein are methods of reducing contamination by one or more toxins in a biological substance comprising contacting the biological substance with an effective amount of a sorbent capable of sorbing one or more non-toxic subunits, wherein when two or more of those subunits are combined forms a toxin, wherein the sorbent comprises a plurality of pores ranging from 50 Å to 40,000 Å with a pore volume of 0.5 cc/g to 5.0 cc/g and a size of 0.05 mm to 2 cm, and sorbing the one or more non-toxic subunits. Also provided herein are methods of treating contamination by one or more toxins in a subject in need thereof comprising contacting a biological substance of the subject with an effective amount of a sorbent capable of sorbing one or more non-toxic subunits, wherein when two or more of those subunits are combined forms a toxin, wherein the sorbent comprises a plurality of pores ranging from 50 Å to 40,000 Å with a pore volume of 0.5 cc/g to 5.0 cc/g and a size of 0.05 mm to 2 cm, and sorbing the one or more non-toxic subunits.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

Figure 1:
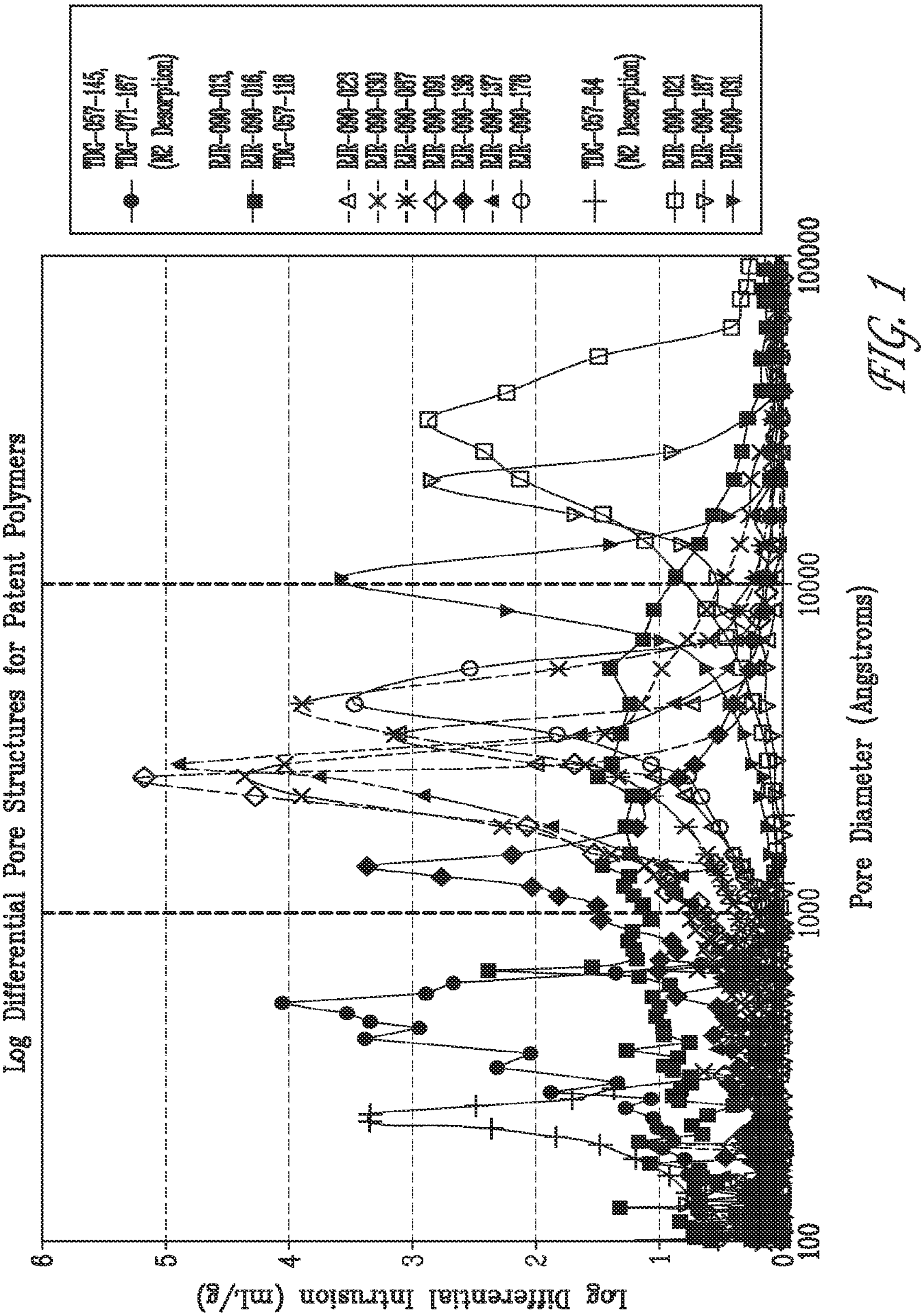
FIG. 1 illustrates pore volume of the sorbent plotted as a function of the pore diameter of the sorbent on a log scale.

The present invention may be understood more readily by reference to the following detailed description taken in connection with the accompanying figures and examples, which form a part of this disclosure. It is to be understood that this invention is not limited to the specific materials, devices, methods, applications, conditions or parameters described and/or shown herein, and that the terminology used herein is for the purpose of describing particular embodiments by way of example only and is not intended to be limiting of the claimed invention. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further reference to values stated in ranges include each and every value within that range.

The following definitions are intended to assist in understanding the present invention:

The term "anti-microbial agent" includes antibacterial agents, anti-viral agents, antifungal agents, antiseptics and the like. Suitable antimicrobial agents include, but are not limited to isoniazid, rifampin, pyrazinamide, ethambutol, erythromycin, vancomycin, tetracycline, chloramphenicol, sulfonamides, gentamicin, amoxicillin, penicillin, streptomycin, p-aminosalicyclic acid, clarithromycin, clofazimine, minocycline, sulfonamides, ethionamide, cycloserine, kanamycin, amikacin, capreomycin, viomycin, thiacetazone, rifabutin and the quinolones, such as ciprofloxacin, ofloxacin and sparfloxicin, rifampin, oseltamivir, acyclovir, lamivudine, azole antifungals, echinocandins, and others. Antibacterial agents includes but are not limited to β-lactam antibacterial agents including, e.g. carbenicillin; ampicillin, cloxacillin, oxacillin and pieracillin, cephalosporins and other cephems including, e.g. cefaclor, cefamandole, cefazolin, cefoperazone, ceftaxime, cefoxitin, ceftazidime, ceftriazone and carbapenems including, e.g., imipenem and meropenem; and glycopeptides, macrolides, quinolones (e.g. nalidixic acid), tetracyclines, and aminoglycosides (e.g. Gentamicin and Paromomycin).

The term "biocompatible" is defined to mean the sorbent is capable of coming in contact with physiologic fluids, living tissues, or organisms without producing unacceptable clinical changes during the time that the sorbent is in contact with the physiologic fluids, living tissues, or organisms. In some embodiments, it is intended that the sorbent is tolerated by the gut and alimentary canal of the organism. The sorbents of the present invention are preferably non-toxic. A biocompatible sorbent may be a biodegradable polymer, a resorbable polymer, or both.

The term "microbe" includes a bacteria, viruses, fungi and parasites.

The term "toxin" is used to mean a substance identified as an etiological agent linked to a negative clinical outcome. Toxins include toxin subunits, toxin precursors, and virulence factors. The toxin can be from a biological source such as bacteria, viruses, fungi, parasites, plants or animals. A toxin may be pre-formed or may only become toxic once in the presence of a biological substance. For example, botulinum toxin (one of 7 subtypes) is made by the bacterium, *Clostridium botulinum*, often under anaerobic conditions, such as in canned goods. When ingested, this pre-formed botulinum toxin is one of the most potent toxins known, blocking neuromuscular transmission by inhibiting acetylcholine release in the synapse, causing paralysis and respiratory failure. Ricin toxin, made from castor beans, is another example of a pre-formed toxin that when inhaled, injected, or ingested can be fatal. Amatoxins, from mushrooms, and aflatoxin, which are mycotoxins produced by strains of the fungus species, *Aspergillus*, are examples of other pre-formed toxins. A toxin may also be made within the body, often by microbes, but can be made by the patient's own cells, as occurs in viral infection. Examples include toxins TcdA and TcdB, made by *Clostridium dificile* bacterium and released into the intestinal lumen that kills cells in the gastrointestinal tract, leading to severe, potentially life-threatening diarrhea. Another example is Shiga-like toxin or verotoxin that is produced by certain strains of *Escherichia coli* that are frequently transmitted by contaminated undercooked meat, vegetables, or fruit and cause food-borne illness. Verotoxin is produced by the bacterium in the intestinal lumen, but then is absorbed into the bloodstream, where it is taken up by vascular endothelial cells, killing them. Verotoxin preferentially targets the glomerulus, causing renal failure and can lead to fatal hemolytic uremic syndrome. Yet another example is the NSP4 toxin, produced by a patient's own cells following gastrointestinal infection with the virus, rotavirus. Rotavirus is the most common cause of severe diarrhea in infants, killing more than 600,000 patients a year. NSP4 acts as an enterotoxin, activating ion channels in the colonic epithelium, causing a profuse secretory diarrhea, without causing any structural damage. An excess of a normally non-toxic substance, can also become a toxin when present at high concentrations. An example includes cytokines, which are normally produced proteins of the immune system that at low levels are important for immune system function, but at high levels become inflammatory toxins that cause cell death, severe inflammation, and organ dysfunction. Toxins can also be formed by the metabolism of a non-toxic precursor or protoxin. One example is amyloid precursor protein, a non-toxic protein produced in the body that when cleaved by enzymes called secretases, can form the fragment beta-amyloid protein, a toxin that can lead to the formation of amyloid plaques, the pathogenic root cause of Alzheimer's disease. Non-toxic subunits or precursors can also become toxins when combined with each other. An example of this is the production of lethal factor, edema factor, and protective antigen by *Bacillus anthracia*, which is responsible for the disease anthrax. By themselves, they are non-toxic, but when combined together and taken into the cell, these subunits form the deadly toxins, lethal toxin and edema toxin, causing cell death and cell lysis. Another example is *Staphylococcus aureus* alpha toxin, which is not toxic as a monomer, but becomes a potent hemolytic toxin when seven monomers assemble into a pore forming complex. A substance may also have no toxic effects when in one location in the body, but may become a toxin when placed in another part of the body. An example of this is the gram negative bacterial endotoxin, lipopolysaccharide, which has little toxicity in the intestinal lumen, but causes septic shock if it escapes into the bloodstream. Toxins can also be common enzymes, such as lipases, amylases, trypsin, hyaluronidase, collagenase and others that cause cell or tissue damage when not appropriately regulated, or when active in a region of the body that is not protected against their enzymatic action. When these substances help the spread or virulence of pathogens in the body, they are classified as "virulence factors". These are examples and not meant to be limiting.

The term "gastrointestinal lumen" or "lumen" refers to the space or cavity within a gastrointestinal tract.

The term "gastrointestinal disorder" as used herein includes gastritis, Ménétrier disease, gastrointestinal ulceration, gastroenteritis, gastrointestinal inflammatory disease, enteric infection, gut-mucosal injury, inflammatory bowel disease, celiac disease, and the like.

As used herein, the term "sorbent" includes adsorbents and absorbents.

As used herein, the term "physiologic fluids" are liquids that originate from the body and can include, but are not limited to, nasopharyngeal, oral, esophageal, gastric, pancreatic, hepatic, pleural, pericardial, peritoneal, intestinal, prostatic, seminal, vaginal secretions, as well as tears, saliva, lung or bronchial secretions, mucus, bile, blood, lymph, plasma, serum, synovial fluid, cerebrospinal fluid, urine, and interstitial, intracellular, and extracellular fluid, such as fluid that exudes from burns or wounds.

As used herein, "carrier fluids" are exogenously administered liquids that include, but are not limited to, liquids administered orally, via a feeding tube, peritoneally, or rectally such as an enema or colonic wash.

As used herein, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Unless defined otherwise, all other technical and scientific terms used herein have the same meaning as commonly understood by one of ordinary skill in the art pertinent to the methods and compositions described. As used herein, the following terms and phrases have the meanings ascribed to them unless specified otherwise.

In addition, various references are identified below and are incorporated by reference in their entirety.

The present invention is based in-part on the discovery that by engineering pore structure that is defined by the ratio of pore size range to pore volume, biocompatible sorbents compositions can be manufactured that sorb toxins, toxin precursors, toxin subunits, or virulence factors, collectively termed "toxins" of a broad range of sizes irrespective of other physical characteristics. The biocompatible sorbents can be used to inhibit or reduce contamination by one or more toxins when introduced into a biological substance, generally mammalian, and particularly human. However, the biological substance can also be a manufactured substance that supports proliferation or maintenance of a microorganism. The sorbent compositions will be useful in reducing toxins while working in conjunction with anti-microbial agents that kill or halt the growth of microbes that are either directly producing the toxin or causing the toxin to be produced. The sorbent compositions will be also useful in situations where other treatments may not be unavailable for a variety of reasons. For example, the sorbents can be used in cases where the toxin has not been definitively identified. Another instance where the present biocompatible sorbent and methods may be useful is when a toxin is identifiable, but not yet sufficiently typed or cultured for targeted treatments. Another instance is where anti-microbials cannot be used, for fear of greater toxin release when the microbe dies that will worsen the patient's condition.

The present biocompatible sorbent compositions are comprised of a plurality of pores. The biocompatible sorbents are designed to adsorb a broad range of toxins from less than 1 kDa to 1,000 kDa. While not intending to be bound by theory, it is believed the sorbent acts by sequestering molecules of a predetermined molecular weight within the pores. The size of a molecule that can be adsorbed by the polymer will increase as the pore size of the polymer increases. Conversely, as the pore size is increased beyond the optimum pore size for adsorption of a given molecule, adsorption of said protein may or will decrease.

In one embodiment a porous polymer that absorbs small to midsize protein molecules equal to or less than 50,000 Daltons (50 kDa) and excludes absorption of large blood proteins comprises the pore structure such that the total pore volume of pore size in the range of 50 Å to 40,000 Å are in the range of 0.5 cc/g to 5.0 cc/g dry sorbent. The sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 100 Å to 1,000 Å (pore diameter) of the sorbent is smaller than 3:1.

In another embodiment a porous polymer that optimally absorbs midsize to large size protein molecules of approximately 300,000 Daltons and excludes or minimizes absorption of very large blood proteins comprises the pore structure such that the total pore volume of pore size in the range of 50 Å to 40,000 Å are in the range of 0.5 cc/g to 5.0 cc/g dry sorbent. The sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 1,000 Å to 10,000 Å (pore diameter) of the sorbent is smaller than 2:1.

In another embodiment a porous polymer that optimally absorbs very large size protein molecules equal to or less than 1,000,000 Daltons and excludes or minimizes absorption of very large blood proteins comprises the pore structure such that the total pore volume of pore size in the range of 50 Å to 40,000 Å are in the range of 0.5 cc/g to 5.0 cc/g dry sorbent. The sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 10,000 Å to 40,000 Å (pore diameter) of the sorbent is smaller than 3:1.

The biocompatible sorbent is introduced into a biological substance. The term biological substance includes substances found in vivo, generally from a mammal such as dogs, cats, rabbits, cows, sheep, horses, pigs and goats, preferably a human. The biological substances are, for example, cells, or physiologic fluids such as saliva, nasopharyngeal, blood, plasma, serum, gastrointestinal fluid, bile, cerebrospinal fluid, pericardial, vaginal fluid, seminal fluid, prostatic fluid, peritoneal fluid, pleural fluid, urine, synovial fluid, interstitial fluid, intracellular fluid or cytoplasm, lymph, bronchial secretions, mucus, or vitreous or aqueous humor. The term also includes substances that support proliferation or maintenance of eukaryotic or prokaryotic cells, viruses, fungi, or protozoa ex vivo, such as culture media, biological matrices, eggs and the like. The biocompatible sorbent and biological substance can be introduced and admixed either in vivo or ex vivo.

Toxins are most commonly organic substances such as proteins, peptides, carbohydrates, lipids, nucleic acids, and combinations thereof (e.g. multimeric or multi-subunit proteins, glycoproteins, glycolipids, lipoproteins, etc.). Toxins can also include organic chemicals (e.g. alkaloids), as well as certain inorganic molecules (e.g. cyanide).

Toxins can be produced by a wide range of organisms. For example, toxins can be produced by micro-organisms such as bacteria, viruses, fungi and parasites. Toxins can also be formed by macro-organisms such as insects, fish, crustaceans, shellfish, amphibians, reptiles, birds, and mammals. Toxins can also be produced by vegetative matter such as plants, algae, and phytoplankton. Viruses typically contain the genetic code, via DNA or RNA, or other nucleic acid sequences, to direct the cells they infect to manufacture viral proteins, including toxins. Many toxins can also be found environmentally, the product of natural processes. Toxins can be formed by the assembly and/or modification of subunits that may or may not be toxic by themselves. Toxins may be non-toxic substances at low concentrations, but becomes toxic at higher concentrations. Some toxins may be location specific. Toxins can also be byproducts of metabolism of non-toxic precursors. Toxins can also be artificially synthesized and manufactured (e.g. biowarfare applications, etc).

Exogenous toxins can be ingested, injected, inhaled, absorbed by the skin or mucosal surfaces, such as the buccal or oral mucosa, the sublingual mucosa, the nasal mucosa, the sinuses, the nasopharynx, the oropharynx, the respiratory tract, the gastrointestinal tract, the urogenital tract, and the eye mucosa. Endogenous toxins can be produced anywhere in the body, such as in the blood, the gastrointestinal tract, the respiratory tract, the urogenital tract, within tissues, and within body cavities. Often, endogenous toxins can act locally, by disrupting local biologic processes or causing local disease, or toxins can act systemically, disrupting systemic biologic processes, causing systemic disease or organ dysfunction. Non-toxic precursors can also be absorbed from the environment or produced in the body, and are then converted in the body into toxins via metabolism or other modification.

Toxins can cause pathology via a number of different mechanisms. Some cause the direct killing of cells. For example, brown recluse spider venom contains a number of toxins that make it both cytolytic and hemolytic. These toxins are enzymes such as hyaluronidase, deoxyribonuclease, ribonuclease, alkaline phosphatase, and lipase. Sphingomyelinase D is thought to be the protein component responsible for most of the tissue destruction and hemolysis caused by brown recluse spider envenomation. The intense inflammatory response mediated by arachidonic acid, prostaglandins, and chemotactic infiltration of neutrophils is amplified further by an intrinsic vascular cascade involving the mediator C-reactive protein and complement activation. These and other factors contribute to the local and systemic reactions of necrotic arachnidism. Others act by causing a disruption in normal cellular physiology. For example, anthrax edema factor binds with protective antigen, to cause direct cell death.

One of the most common sources of toxins are from enteric pathogens such as *Clostridium difficile, Enterohemorrhagic E. coli* (EHEC)) such as *E. coli* OE157:H7 or *E. coli* O104:H4, *Vibrio cholera, Shigella dysenteriae*, and rotovirus. These toxins can damage or kill cells of the gastrointestinal mucosa, and can alter gastrointestinal homeostasis, often resulting in diarrhea and vomiting that can lead to dehydration, malabsorption, and potentially even death, particularly in the young, the elderly, and immunocompromised subjects. These toxins can result in more serious complications such as colitis, bloody diarrhea, gastrointestinal bleeding, a decrease in immune system function, toxic megacolon, intestinal perforation, shock, sepsis and death. A compromise of the gastrointestinal mucosa caused by infection and toxins, can further lead to the translocation of bacteria and toxins, such as endotoxin, from the intestinal tract, into the blood or body, which can trigger or exacerbate sepsis. According to the CDC, there were 221,226 cases of cholera in 45 countries in 2009, causing approximately 5,000 deaths. These were caused predominantly by toxigenic, or toxin producing, strains of cholera serogroups O1 and O139, that produced large amounts of cholera toxin. Some toxins can be absorbed from the gastrointestinal tract, such as botulinum, or shiga-like toxin (STX-1), and distributed to different parts of the body via blood, or lymph, causing disease.

Enteric pathogens are commonly found in the environment and include bacteria, viruses, parasites and plants. Pathogenesis may be directly related to the organism (e.g. *Yersinia enterocolitica*, Norwalk virus), related to a toxin produced by organism (e.g. *Clostridium difficile*, Enterotoxigenic *E. coli* (ETEC)), caused by changes in cellular function resulting in release of pro-inflammatory cytokines (e.g., Enteropathogenic *E. coli* (EPEC), *Camplylobacter jejuni*), or a combination of these of mechanisms (e.g. *Vibrio cholera, Shigella dysenteriae*).

Embodiments of the present invention can be used to inhibit or reduce contamination by toxins across a broad range of molecular weights and a pre-formed toxin or a toxin formed in the presence of the biological substance. An example of a toxin formed in the presence of a biological substance is a bacterial endotoxin, such as lipopolysaccharide (LPS). The appearance of LPS in the host bloodstream is believed to lead to the endogenous production of a variety of host factors that directly and indirectly mediate the toxicity of LPS. These host-derived mediators include many now well-recognized inflammatory cytokines, endocrine hormones, and a number of other endogenous factors such as leukotrienes and platelet activating factor. Cytokines such as TNF-α, IL-1, and IFN-γ are released from stimulated macrophages and T lymphocytes as a result of infection by a variety of microorganisms, including bacteria, viruses, fungi, and parasites. The interacting factors comprise the cytokine cascade. TNF-alpha has been observed to stimulate production of other types of cytokines. IL-1 induces responses observed in inflammation in general, such as fever, increase of leukocytes, activation of lymphocytes, and induction of biosynthesis of acute phase protein in liver. However, at high levels, these cytokines and others can be inflammatory toxins and cause undesirable effects such as capillary leak, cell death via apoptosis, hemodynamic instability, organ dysfunction, and cachexia.

As another example, in bacterial infections, cytokines such as IL-8 act as a signal that attracts white blood cells such as neutrophils to the region of cytokine expression. In general, the release of enzymes and superoxide anions by neutrophils is essential for destroying the infecting bacteria. However, if cytokine expression causes neutrophils to invade, for example, the lungs, release of neutrophil enzymes and oxygen radicals can result in the development of adult respiratory distress syndrome (ARDS), which can be lethal.

In certain embodiments, the toxin is from one or more diverse biological sources. Biological sources can comprise one or more bacteria, viruses, fungi, or parasites as shown in Table 1, a non-exclusive list of toxins, toxin subunits, and their representative pathogens.

TABLE 1

Toxins

| Exotoxin or Enterotoxin | Genus | Species | Toxin MW |
|---|---|---|---|
| Enterotoxigenic STa and STb (heat stable enterotoxin) | | Enterotoxigenic E. coli (ETEC) | 2 kDa and 5.2 kDa, respectively |
| Staphylococcal toxin B | Staphylococcus | S. aureus | 23-29 kDa |
| Alpha toxin | Staphylococcus | S. aureus | 33 to 85 kDa |
| Toxic shock syndrome toxin (TSST-1) | Staphylococcus | S. aureus | 22 kDa |
| Clostridium perfringens enterotoxin | Clostridium | C. perfringens | 35 kDa |
| C. perfringens Alpha toxin | Clostridium | C. perfringens | 43 kDa |
| Aerolysin | Aeromonas | A. hydrophila | 52 KDa |
| Pseudomonas Exotoxin A | Pseudomonas | P. aeruginosa | 66 kDa |
| Shiga-like toxin (STX-1, STX-2; verotoxin) | Escherichia | Enterohemorrhagic E. coli (EHEC) | 69 kDa |
| Shiga toxin | | Shigella dysenteria | 70 kDa |
| Cholera Toxin | Vibrio | Vibrio cholerae | 84 kDa |
| Enterotoxigenic LT (heat labile enterotoxin) | Escherichia | Enterotoxigenic E. ecoli (ETEC) | 86 kDa |
| Lipopoly-saccharide Endotoxin | Gram negative bacteria | | 10 kDa, up to 1000 kDa aggregated |
| Lipoteichoic acid Endotoxin | Gram positive bacteria | | 10 kDa |
| Cyanotoxins | Cyanobacteria | | Varied sizes |
| Pertussis toxin | Bordetella | B. pertussis | 105 kDa |
| Tetanus Toxin | Clostridium | C. tetani | 150 kDa |
| Botulinum toxin | Clostridium | C. botulium | 150 kDa |
| C. diff toxin B (TcdB) | Clostridium | C. difficile | 250-270 kDa |
| C. diff toxin A (TcdA) | Clostridium | C. difficile | 308 kDa |

Table 2 is a non-exclusive list of viral toxins where the present sorbent can be used to reduce or inhibit contamination of a biological substance.

TABLE 2

VIRUS

| Toxin | Family | Virus | MW |
|---|---|---|---|
| Rotavirus NSP4 toxin | Reoviridae | Rotavirus | 28 kDa |

Table 3 is a non-exclusive list of fungal toxins where use of the present sorbent can reduce or inhibit contamination of a biological substance.

TABLE 3

FUNGUS

| Toxin | Genus | Species | MW |
|---|---|---|---|
| adhesins | Candida | C. albicans, C. esophagitis | |
| Aflatoxin and other mycotoxins | Aspergillus | A. flavus A. parasiticus | 312-346 Daltons |
| Amatoxin | Amanita | A. phalloides, A. brunnescens | 900 Daltons |

Table 4 is a non-exclusive list of plant-derived toxins where use of the present sorbent can reduce or inhibit contamination of a biological substance.

TABLE 4

PLANT

| Toxin | Common Name | Genus and Species | MW |
|---|---|---|---|
| Ricin toxin | Castor Bean | Ricinis communis | 65 kDa |
| Pyrrolizidine Alkaloids | Legumes, fescue grass, contaminated milk and flour | | |
| Phytohaemagglutinin | Kidney Beans | Phaseolus vulgaris | |
| Vomitoxin | Grains | | |

Table 5 is a non-exclusive list of animal-derived toxins where use of the present sorbent can reduce or inhibit contamination of a biological substance.

TABLE 5

ANIMAL DERIVED

| Toxin | | Example of Source | MW |
|---|---|---|---|
| Ciguatera fish toxin | | Grouper, red snapper, amberjack, barracuda | |
| Tetrodotoxin | | Puffer fish | |
| Scombroid | (Histamine) | Fish: bluefin, tuna, skipjack, marlin, mackerel | |
| Shellfish toxin | | Mussels, scallops, shrimps, oysters (shellfish) | |
| Cytokines | (TNF-α, IL-1, IL-6, IL-8, IL-10) | Subject's cells, egg cells | 10 kDa, up to 1000 kDa aggregated |
| Hemoglobin | | | |

Furthermore, the compositions of biocompatible sorbents can comprise a mixture of sorbents with different pore structures. Such a mixture will be advantageous, for example, when the pathogen has not been definitively identified or there is reason to suspect there are multiple pathogens associated with the gastroenteritis, such as with the ingestion of contaminated water.

In another example, the present methods and sorbents can be used in treating infections with *Clostridium difficile* via oral or rectal administration. *C. difficile* is commonly acquired in hospitals worldwide and other long-term healthcare settings. It is a leading cause of severe diarrhea in these institutions. In the hospital setting the consequences include, longer stays, more readmissions and higher costs. (Glouliouris et al., *Clin. Med.*, 11:75-79, 2011). *C. difficile* spores are excreted in large numbers by patients and contamination can survive for months or years. The bacteria are generally inhibited by the normal flora of the gastrointestinal system, but an imbalance or disruption in the colonic flora, allows for *C. difficile* to proliferate and produce toxins resulting in diarrhea, and possibly fever and colitis. The available treatment is metronidazole and vancomycin, but reoccurrence is common because full recovery requires re-establishing the normal intestinal flora. *C. difficile* produce two toxins, Toxin A and Toxin B, both of which are pathogenic. (Lyerly et al., *Clin. Microbiol. Rev.*, 1(1):1-18, 1988) The proteins are quite large, both Toxins A and B are greater than 250,000 under reduced conditions and have been described ranging from 400,000 to 600,000 Daltons for Toxin A (Krivan and Wilkins, *Infect. Immun.*, 55:1873-1877, 1987; Bano et al., *Rev. Infect. Dis.* 6:S11-S20 1984; Bano et al., *Biochem. Int.*

2:629-635, 1981), and 360,000 to 500,000 Daltons for Toxin B (Lyerly et al., *Infect. Immun.* 54:70-76, 1986).

In another example, the present methods and sorbents can be used in treating bacterial toxins in the blood using a hemocompatible sorbent in an extracorporeal hemoperfusion system. Standard hemodialysis, hemofiltration and charcoal hemoperfusion are not capable of removing toxins larger than approximately 10 kDa. High molecular weight cutoff filters, and mid-molecular weight sorbent cartridges are not ideally suited for broad, particularly large (>60 kDa) toxin removal. This sorbent system, in conjunction with antibiotics, could be used to remove pathogen derived toxins from blood, plasma or scrum in a range of less than 1 kDa to more than 400 kDa. Examples of infections that also produce blood-borne toxins include *Staphylococcus aureus* and methicillin-resistant *Staphlococus aureus* (MRSA) that produce alpha toxin or toxic shock syndrome toxin-1; enterohemorrhagic *E. coli* enteral infection associated with systemic shiga-like toxin toxemia; *Clostridium perfringens* infection with alpha toxin production causing necrotizing fasciitis; Aeromonas wound infection with aerolysin toxin production, and others.

In some embodiments, the sorbent comprises a coated polymer comprising at least one crosslinking agent and at least one dispersing agent.

Some preferred coated polymers comprise at least one crosslinking agent and at least one dispersing agent. Suitable dispersing agents include hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly(diethylaminoethyl acrylate), poly(vinyl alcohol), poly(N-vinylpyrrolidinone), salts of poly(methacrylic acid), and salts of poly(acrylic acid) and mixtures thereof.

Suitable crosslinking agents include divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triiacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, divinylformamide and mixtures thereof. Preferably, the polymer is developed simultaneously with the formation of the coating, such that the dispersing agent gets chemically bound to the surface of the polymer.

The use of an organic solvent as a porogen or pore-former, and the resulting phase separation induced during polymerization yield porous polymers. Some preferred porogens are Benzyl alcohol, Cyclohexane, Cyclohexanol, Cyclohexanol/toluene mixtures, Cyclohexanone, Decane, Decane/toluene mixtures, Di-2-ethylhexylphosphoric acid, Di-2-ethylhexyl phthalate, 2-Ethyl-1-hexanoic acid, 2-Ethyl-1-hexanol, 2-Ethyl-1-hexanolin-heptane mixtures, 2-Ethyl-1-hexanol/toluene mixtures, Isoamyl alcohol, n-Heptane, n-Heptane/ethylacetate, n-Heptane/isoamyl acetate, n-Heptane/tetraline mixtures, n-Heptane/toluene mixtures, n-Hexane/toluene mixtures, Pentanol, Poly(styrene-co-methyl methacrylate)/dibutyl phthalate, Polystyrene/2-ethyl-1-hexanol mixtures, Polystyrene/dibutyl phthalate, Polystyrene/n-hexane mixtures, Polystyrene/toluene mixtures, Toluene, Tri-n-butylphosphate, 1,2,3-Trichloropropane/2-ethyl-1-hexanol mixtures, 2,2,4-Trimethyl pentane (isooctane), Trimethyl pentane/toluene mixtures, Poly(propylene glycol)/toluene mixtures Poly(propylene glycol)/cyclohexanol mixtures, and Poly(propylene glycol)/2-Ethyl-1-hexanol mixtures Preferred sorbents comprise polymers derived from one or more monomers selected from divinylbenzene and ethylvinylbezene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythritol dimethacrylate, pentaerythritol trimethacrylate, pentaerythritol tetramethacrylate, pentaerythritol diacrylate, pentaerythritol triiacrylate, pentaerythritol tetraacrylate, dipentaerythritol dimethacrylate, dipentaerythritol trimethacrylate, dipentaerythritol tetramethacrylate, dipentaerythritol diacrylate, dipentaerythritol triacrylate, dipentaerythritol tetraacrylate, divinylformamide and mixtures thereof.

Some preferred polymers comprise ion exchange polymers.

Some preferred polymers comprise cellulosic polymers. Suitable polymers include cross-linked dextran gels such as Sephadex™.

Certain preferred polymers comprise porous highly crosslinked styrene or divinylbenzene copolymers. Some of these copolymers comprise a macroporous or mesoporous styrene-divinylbenzene-ethylstyrene copolymer subjected to a partial chloromethylation to a chlorine content of up to 7% molecular weight. Other of these polymers are a hypercrosslinked polystyrene produced from crosslinked styrene copolymers by an extensive chloromethylation and a subsequent post-crosslinking by treating with a Friedel-Crafts catalyst in a swollen state. Yet other of these polymers are a hypercrosslinked polystyrene produced from crosslinked styrene copolymers by an extensive additional post-crosslinking in a swollen state with bifunctional crosslinking agents selected from the group comprising of monochlorodimethyl ether and p-xylilene dichloride Some polymers useful in the practice of the invention are hydrophilic self-wetting polymers that can be administered as dry powder containing hydrophilic functional groups such as, amines, hydroxyl, sulfonate, and carboxyl groups.

Certain polymers useful in the invention are macroporous polymers prepared from the polymerizable monomers of styrene, divinylbenzene, ethylvinylbenzene, and the acrylate and methacrylate monomers such as those listed below by manufacturer. Rohm and Haas Company, (now part of Dow Chemical Company): (i) macroporous polymeric sorbents such as Amberlite™ XAD-1, Amberlite™ XAD-2, Amberlite™ XAD-4, Amberlite™ XAD-7, Amberlite™ XAD-7HP, Amberlite™ XAD-8, Amberlite™ XAD-16, Amberlite™ XAD-16 HP, Amberlite™ XAD-18, Amberlite™ XAD-200, Amberlite™ XAD-1180, Amberlite™ XAD-2000, Amberlite™ XAD-2005, Amberlite™ XAD-2010, Amberlite™ XAD-761, and Amberlite™ m XE-305, and chromatographic grade sorbents such as Amberchrom™ m CG 71,s,m,c, Amberchrom™ CG 161,s,m,c, Amberchrom™ CG 300,s,m,c, and Amberchrom™ CG 1000,s,m,c. Dow Chemical Company: Dowex™ Optipore™ L-493, Dowex™ Optipore™ V-493, Dowex™ Optipore™ V-502, Dowex™ Optipore™ L-285, Dowex™ Optipore™ L-323, and Dowex™ m Optipore™ m V-503. Lanxess (formerly Bayer and Sybron): Lewatit™ VPOC 1064 MD PH, Lewatit™ VPOC 1163, Lewatit™ OC EP 63, Lewatit™ S 6328A, Lewatit™ OC 1066, and Lewatit™ 60/150 MIBK. Mitsubishi Chemical Corporation: Diaion™ HP 10, Diaion™ HP 20, Diaion™ HP 21, Diaion™ HP 30, Diaion™ HP 40, Diaion™ HP 50, Diaion™ SP70, Diaion™ SP 205, Diaion™ SP 206, Diaion™ SP 207, Diaion™ SP 700, Diaion™ SP 800, Diaion™ SP 825, Diaion™ SP 850, Diaion™ SP 875, Diaion™ HP 1MG, Diaion™ HP 2MG, Diaion™ CHP 55A, Diaion™ CHP 55Y, Diaion™ CHP 20A, Diaion™ CHP 20Y, Diaion™ CHP 2MGY, Diaion™ CHP 20P, Diaion™ HP 20SS, Diaion™ SP 20SS, and Diaion™ SP 207SS. Purolite Company: Purosorb™ AP 250 and Purosorb™ AP 400.

The present invention does not rely on charge or a ligand-receptor complex binding reaction to inhibit or reduce pathogen toxicity. A polymer using acid functional group(s) attached to the polymer backbone to bind *Clostridium difficile* Toxin A and Toxin B is described by Bacon Kurtz et al. (U.S. Pat. No. 6,890,523). The interaction in Kurtz is ionic where a hydrophobic or hydrophilic group attached to the polymer binds the toxin. Chamot el al. (US Patent Application 2006/009169) describe using inorganic polymer particles linked to a toxin binding moiety comprised of oligosaccharide sequences that bind *C. difficile* Toxin A and Toxin B. Also described is a toxin binding surface pore size 2× larger than toxin diameter. Chamot described oligosaccharide moieties that bind toxins to form a ligand/receptor-like complex.

The polymer materials used as the sorbent are generally not metabolizable by human and animal, but may be synthesized from materials characterized as being a biodegradable polymer, a resorbable polymer, or both. Certain polymers may be irregular or regular shaped particulates such as powders, beads, or other forms with a diameter in the range of 0.1 micron meters to 2 centimeters.

The polymers used in the instant invention preferably have a biocompatible and hemocompatible exterior surface coatings but are not absolutely necessary, especially in certain circumstances, such as oral or rectal administration. Certain of these coatings are covalently bound to the polymer particle (beads, for example) by free-radical grafting. The free-radical grafting may occur, for example, during the transformation of the monomer droplets into polymer beads. The dispersant coating and stabilizing the monomer droplets becomes covalently bound to the droplet surface as the monomers within the droplets polymerize and are converted into polymer. Biocompatible and hemocompatible exterior surface coatings can be covalently grafted onto the preformed polymer beads if the dispersant used in the suspension polymerization is not one that imparts biocompatibility or hemocompatibility. Grafting of biocompatible and hemocompatible coatings onto preformed polymer beads is carried out by activating free-radical initiators in the presence of either the monomers or low molecular weight oligomers of the polymers that impart biocompatibility or hemocompatibility to the surface coating.

The route of administration can be systemic or localized. In certain embodiments, the compositions may be given orally, rectally or via a feeding tube. The sorbent can be supplied as a dry powder or other dry particulate capable of being wetted externally or internally in the alimentary canal, including in the gastric or enteric environment, with or without the addition of wetting agents such as ethyl or isopropyl alcohol, potable liquids such as water, or other carrier fluid. Other possible routes of administration include subcutaneous or transdermal delivery. In some embodiments, administration is topical. Such methods include ophthalmic administration, administration to skin or wounds, direct administration into a body cavity or joint, and delivery to mucous membranes such as nasal, oral, vaginal and rectal delivery or other delivery to the alimentary canal. In some embodiments, the treatment is extracorporeal. Extracorporeal administration would include removal of inflammatory mediators from blood or physiologic fluids by circulating the fluids through a device containing sorbent and returning it back to the body. In some embodiments, such methods include local or systemic administration through a parenteral route. Parenteral administration includes intravenous, intraarterial, subcutaneous, intraperitoneal or intramuscular injection or infusion; or intracranial (including intrathecal or intraventricular, administration).

The sorbent may be formulated as for example, a powder, a tablet, a capsule, a solution, a slurry, an emulsion, a suppository, or in a food substance. The sorbent may be packaged in portable bottles, vials, blister packs, bags, pouches, or other container that allows for either single or multiple dosages. Depending on the use, the sorbent may be sterile or non-sterile. The polymer may be sterilized by standard methods. Such methods are well known to those skilled in the art. The therapeutically effective amount can be administered in a series of doses separated by appropriate time intervals, such as hours. The compositions of the instant invention may be administered by methods well known to those skilled in the art.

The foregoing description is provided for the purpose of explanation and is not to be construed as limiting the invention. While the invention may have been described with reference to preferred embodiments or preferred methods, it is understood that the words which have been used herein are words of description and illustration, rather than words of limitation. Furthermore, although the invention has been described herein with reference to particular materials structure, methods, compositions and embodiments, the invention is not intended to be limited to the particulars disclosed herein, as the invention extends to all structures, methods, compositions and uses that are within the scope of the appended claims. Further, several advantages have been described that flow from the composition and methods; the present invention is not limited to composition and methods that encompass any or all of these advantages. Those skilled in biocompatible polymer technology, having the benefit of the teachings of this specification, may effect numerous modifications to the invention as described herein, and changes can be made without departing from the scope and spirit of the invention as defined by the appended claims. Furthermore, any features of one described embodiment can be applicable to the other embodiments described herein. For example, any features or advantages related to the design of the biocompatible polymers with respect to discussion of a particular toxin absorption embodiment can be applicable to any of the other toxin absorption embodiments described herein.

The invention is further illustrated by the following non-limiting examples.

EXAMPLES

Examples 1-18

Eighteen porous polymeric adsorbents are characterized for their pore structures and their syntheses are described in Examples 1-18. The pore structure characterization is given in Example 19.

The synthesis process consists of (1) preparing the aqueous phase, (2) preparing the organic phase, (3) carrying out the suspension polymerization, (4) purifying the resulting porous polymeric adsorbent product (work-up), and (5) addition of a hemo-compatible coating.

The following synthesis procedure is generalized to fit all samples which were made. The synthetic process varied between each polymer sample; refer to Table 6, following the generalized procedure, in order to see specific run conditions for each example.

Reactor Setup. A 5 L or 0.5 L kettle reactor was fitted with an over-head stirrer, a water cooled condenser, a multi-level stirrer blade, a thermocouple, and a bubbler. For the 0.5 L kettles, a gasket was installed between the top lid and bottom kettle. The 5 L set-ups had a baffle plate assembly and two flat rubber gaskets installed between the top lid and bottom kettle. All unused ports were capped with the appropriate plug. Temperature was controlled with a heating mantle which was regulated by a temperature controller fitted with the above-mentioned thermocouple.

Polymerization. Polyvinyl alcohol ("PVA") was dispersed in one half of the water charge at room temperature (RT) and then heated to 70° C. The remaining salts: MSP, DSP, TSP, & Sodium Nitrite were then dissolved in the remainder of the water charge. The PVA solution and salts solution were each added to the reactor and heated to the desired reaction temperature with stirring. The pre-mixed organic phase, including the initiator, was poured into the reactor onto the aqueous phase with the stirring speed set at the revolutions per minute ("rpm") for formation of appropriate droplet size. Once the temperature reached the set-point, the reaction timer was set for 16 hours and started and the reaction was allowed to proceed.

Work-up. Solvent level marked. After cooling, the solvent was siphoned out to the bead level. The beads were then washed 5 times with 50° C.-70° C. water at a rate of 1 bed volume per half hour. The following steps in the work-up were skipped if the polymer was modified (See Table 6). The beads were then washed 3 times with RT methanol at a rate of 1 bed volume per 10 minutes. The polymer was extracted via a soxhlet apparatus overnight. The polymer was steam stripped for 8 hours. After the steam strip was completed, the polymer was rewet in isopropyl alcohol and then sieved with purified water to the desired particle size. The polymer was then dried in an oven at 100° C.

Modification Setup. A kettle reactor was fitted with an over-head stirrer, a multi-level stirrer blade, and a thermocouple. All unused ports were capped with the appropriate plug and one open hose adapter as a vent. A gasket was installed between the top lid and bottom kettle. Temperature was controlled with a heating mantle regulated by a temperature controlled fitted with the above-mentioned thermocouple.

Modification Reaction. Polymer was washed 10 times with isopropyl alcohol at approximately 1 bed volume per hour and then 10 times with purified water at approximately 1 bed volume per hour. The polymer was sieved to the desired particle size and added to the reactor setup. Excess water was siphoned to just above bed level and the charged water was then added. The temperature controller was set to 40° C. and then started. The overhead stirrer was started as well. Each reagent was added while the system was ramping up to the 40° C. set point. Ammonium Persulfate (AMPS) in water was added when the temperature was between 30° C. to 34° C. NNNN-Tetramethylethylenediamine (TMED) and water were added between 35° C. and 36° C. Vinylpyrrolidinone (VP) and water were added between 39° C. and 40° C. The two hour reaction timer was started when the temperature reached 40° C.; the reaction was allowed to proceed. After cooling, the solvent was siphoned out to the bead level. The beads were then washed 3 times with RT water at a rate of 1 bed volume per half hour. The beads were steam stripped for 6 hours. The beads were rewet in isopropyl alcohol and washed ten times in purified $H_2O$. The polymer was then dried in an oven at 100° C.

This process resulted in a clean, dry adsorbent in the form of spherical, porous polymer beads.

TABLE 6

Synthesis Conditions for Examples 1-18.

| | Example 1 TDG-057-64 | Example 2 TDG-071-167 | Example 3 RJR-090-030 | Example 4 TDG-057-118 | Example 5 RJR-090-013 |
|---|---|---|---|---|---|
| Run Conditions | | | | | |
| Kettle Size | 0.5 | 5.0 | 0.5 | 0.5 | 0.5 |
| Reaction Temperature | 80 | 80 | 80 | 87 | 87 |
| Aqueous Phase Charges | | | | | |
| Item | Charge, g | Charge, g | Charge, g | Charge, g | Charge, g |
| Ultrapure Water | 231.26 | 1734.47 | 231.26 | 231.26 | 231.26 |
| Polyvinyl Alcohol (PVA) | 0.68 | 5.06 | 0.68 | 0.68 | 0.68 |
| Monosodium Phosphate (MSP) | 0.71 | 5.34 | 0.71 | 0.71 | 0.71 |
| Disodium Phosphate (DSP) | 2.36 | 17.71 | 2.36 | 2.36 | 2.36 |
| Trisodium Phosphate (TSP) | 1.47 | 10.99 | 1.47 | 1.47 | 1.47 |
| Sodium Nitrite | 0.01 | 0.05 | 0.01 | 0.01 | 0.01 |
| Total | 236.49 | 1773.62 | 236.49 | 236.49 | 236.49 |
| Organic Phase Charges | | | | | |
| Item | Charge, g | Charge, g | Charge, g | Charge, g | Charge, g |
| Divinylbenzene (DVB)(63%) | 129.55 | 592.92 | 83.03 | 83.03 | 83.03 |
| Toluene | 0.00 | 390.48 | 0.00 | 0.00 | 0.00 |
| Isooctane | 0.00 | 448.47 | 0.00 | 0.00 | 0.00 |

TABLE 6-continued

Synthesis Conditions for Examples 1-18.

| | | | | | |
|---|---|---|---|---|---|
| Cyclohexanol | 102.82 | 0.00 | 143.45 | 151.00 | 151.00 |
| PPG | 0.00 | 0.00 | 7.55 | 0.00 | 0.00 |
| Benzoyl Peroxide (BPO)(97%) | 1.32 | 4.49 | 0.84 | 0.84 | 0.84 |
| Total, w/o BPO | 232.37 | 1431.87 | 234.03 | 234.03 | 234.03 |
| Work-Up | | | | | |
| Methanol Washes | 3 | N/A | 3 | 3 | 3 |
| Soxhlet Solvent | Acetone | N/A | Acetone | Acetone | Acetone |
| Sieve Size (μm) | 300-600 | 300-600 | 300-600 | 300-600 | 300-600 |
| Modification | | | | | |
| Amount of Polymer being modified, mL | N/A | 500 | N/A | N/A | 400 |
| Charged Water, mL | N/A | 180 | N/A | N/A | 144 |
| Ammonium Persulfate (AMPS), g | N/A | 3.2 | N/A | N/A | 2.7 |
| in Water for Addition, mL | N/A | 28 | N/A | N/A | 22 |
| NNNN-Tetramethylethylenediamine (TMED), g | N/A | 3.4 | N/A | N/A | 2.9 |
| in Water for Addition, mL | N/A | 14 | N/A | N/A | 11 |
| Vinylpyrrolidinone (VP), g | N/A | 1.7 | N/A | N/A | 1.4 |
| in Water for Addition, mL | N/A | 42 | N/A | N/A | 33 |

| | Example 6 RJR-090-014 | Example 7 RJR-090-016 | Example 8 RJR-090-023 | Example 9 RJR-090-087 | Example 10 RJR-090-091 |
|---|---|---|---|---|---|
| Run Conditions | | | | | |
| Kettle Size | 5.0 | 5.0 | 0.5 | 0.5 | 0.5 |
| Reaction Temperature | 80 | 87 | 80 | 80 | 80 |
| Aqueous Phase Charges | | | | | |
| Item | Charge, g | Charge, g | Charge, g | Charge, g | Charge, g |
| Ultrapure Water | 1500.00 | 1734.47 | 231.26 | 231.26 | 231.26 |
| Polyvinyl Alcohol (PVA) | 4.38 | 5.06 | 0.68 | 0.68 | 0.68 |
| Monosodium Phosphate (MSP) | 4.63 | 5.34 | 0.71 | 0.71 | 0.71 |
| Disodium Phosphate (DSP) | 15.31 | 17.71 | 2.36 | 2.36 | 2.36 |
| Trisodium Phosphate (TSP) | 9.50 | 10.99 | 1.47 | 1.47 | 1.47 |
| Sodium Nitrite | 0.05 | 0.05 | 0.01 | 0.01 | 0.01 |
| Total | 1533.87 | 1773.62 | 236.49 | 236.49 | 236.49 |
| Organic Phase Charges | | | | | |
| Item | Charge, g | Charge, g | Charge, g | Charge, g | Charge, g |
| Divinylbenzene (DVB)(63%) | 1373.00 | 581.23 | 129.55 | 94.73 | 106.38 |
| Toluene | 0.00 | 0.00 | 0.00 | 0.00 | 0.00 |
| Isooctane | 0.00 | 0.00 | 0.00 | 0.00 | 0.00 |
| Cyclohexanol | 0.00 | 1057.01 | 77.11 | 128.47 | 114.14 |
| PPG | 0.00 | 0.00 | 25.70 | 10.42 | 12.68 |
| Benzoyl Peroxide (BPO)(97%) | 6.91 | 5.91 | 1.32 | 0.96 | 1.08 |
| Total, w/o BPO | 1373.00 | 1638.24 | 232.36 | 233.62 | 233.20 |
| Work-Up | | | | | |
| Methanol Washes | N/A | 3 | 3 | 3 | 3 |
| Soxhlet Solvent | N/A | Acetone | Acetone | Acetone | Acetone |
| Sieve Size (μm) | 106-212 | 106-212 | 300-600 | 300-600 | 300-600 |
| Modification | | | | | |
| Amount of Polymer being modified, mL | 500 | 600 | N/A | N/A | N/A |
| Charged Water, mL | 180 | 216 | N/A | N/A | N/A |
| Ammonium Persulfate (AMPS), g | 0.0324 | 4.1 | N/A | N/A | N/A |
| in Water for Addition, mL | 28 | 33 | N/A | N/A | N/A |
| NNNN-Tetramethylethylenediamine (TMED), g | 0.0169 | 4.3 | N/A | N/A | N/A |
| in Water for Addition, mL | 42 | 17 | N/A | N/A | N/A |
| Vinylpyrrolidinone (VP), g | 0.0344 | 2.1 | N/A | N/A | N/A |
| in Water for Addition, mL | 14 | 50 | N/A | N/A | N/A |

TABLE 6-continued

Synthesis Conditions for Examples 1-18.

| | Example 11 RJR-090-136 | Example 12 RJR-090-137 | Example 13 RT-075-14-1 | Example 14 TDG-057-145 |
|---|---|---|---|---|
| Run Conditions | | | | |
| Kettle Size | 0.5 | 0.5 | 5.0 | 5.0 |
| Reaction Temperature | 80 | 80 | 80 | 80 |
| Aqueous Phase Charges | | | | |
| Item | Charge, g | Charge, g | Charge, g | Charge, g |
| Ultrapure Water | 231.26 | 231.26 | 1500.00 | 1734.47 |
| Polyvinyl Alcohol (PVA) | 0.68 | 0.68 | 4.38 | 5.06 |
| Monosodium Phosphate (MSP) | 0.71 | 0.71 | 4.63 | 5.34 |
| Disodium Phosphate (DSP) | 2.36 | 2.36 | 15.31 | 17.71 |
| Trisodium Phosphate (TSP) | 1.47 | 1.47 | 9.50 | 10.99 |
| Sodium Nitrite | 0.01 | 0.01 | 0.05 | 0.05 |
| Total | 236.49 | 236.49 | 1533.87 | 1773.62 |
| Organic Phase Charges | | | | |
| Item | Charge, g | Charge, g | Charge, g | Charge, g |
| Divinylbenzene (DVB)(63%) | 106.38 | 94.73 | 1373.00 | 592.92 |
| Toluene | 0.00 | 0.00 | 0.00 | 390.48 |
| Isooctane | 0.00 | 0.00 | 0.00 | 448.47 |
| Cyclohexanol | 115.73 | 130.21 | 0.00 | 0.00 |
| PPG | 11.10 | 8.68 | 0.00 | 0.00 |
| Benzoyl Peroxide (BPO)(97%) | 1.08 | 0.96 | 6.91 | 4.49 |
| Total, w/o BPO | 233.21 | 233.62 | 1373.00 | 1431.87 |
| Work-Up | | | | |
| Methanol Washes | 3 | 3 | N/A | N/A |
| Soxhlet Solvent | Acetone | Acetone | N/A | N/A |
| Sieve Size (μm) | 300-600 | 300-600 | 300-600 | 45-106 |
| Modification | | | | |
| Amount of Polymer being modified, mL | N/A | N/A | N/A | 2000 |
| Charged Water, mL | N/A | N/A | N/A | 721 |
| Ammonium Persulfate (AMPS), g | N/A | N/A | N/A | 12.9 |
| in Water for Addition, mL | N/A | N/A | N/A | 111 |
| NNNN-Tetramethylethylenediamine (TMED), g | N/A | N/A | N/A | 13.8 |
| in Water for Addition, mL | N/A | N/A | N/A | 55 |
| Vinylpyrrolidinone (VP), g | N/A | N/A | N/A | 6.7 |
| in Water for Addition, mL | N/A | N/A | N/A | 166 |

| | Example 15 RJR-090-178 | Example 16 RJR-090-021 | Example 17 RJR-090-187 | Example 18 RJR-090-031 |
|---|---|---|---|---|
| Run Conditions | | | | |
| Kettle Size | 0.5 | 0.5 | 0.5 | 0.5 |
| Reaction Temperature | 80 | 80 | 80 | 80 |
| Aqueous Phase Charges | | | | |
| Item | Charge, g | Charge, g | Charge, g | Charge, g |
| Ultrapure Water | 231.26 | 231.26 | 231.26 | 231.26 |
| Polyvinyl Alcohol (PVA) | 0.68 | 0.68 | 0.68 | 0.68 |
| Monosodium Phosphate (MSP) | 0.71 | 0.71 | 0.71 | 0.71 |
| Disodium Phosphate (DSP) | 2.36 | 2.36 | 2.36 | 2.36 |
| Trisodium Phosphate (TSP) | 1.47 | 1.47 | 1.47 | 1.47 |
| Sodium Nitrite | 0.01 | 0.01 | 0.01 | 0.01 |
| Total | 236.49 | 236.49 | 236.49 | 236.49 |
| Organic Phase Charges | | | | |
| Item | Charge, g | Charge, g | Charge, g | Charge, g |
| Divinylbenzene (DVB)(63%) | 106.38 | 83.03 | 106.38 | 106.38 |
| Toluene | 0.00 | 0.00 | 0.00 | 0.00 |
| Isooctane | 0.00 | 0.00 | 0.00 | 0.00 |

TABLE 6-continued

| Synthesis Conditions for Examples 1-18. | | | | |
|---|---|---|---|---|
| Cyclohexanol | 109.07 | 113.25 | 104.63 | 107.80 |
| PPG | 17.76 | 37.75 | 22.19 | 19.02 |
| Benzoyl Peroxide (BPO)(97%) | 1.08 | 0.84 | 1.08 | 1.08 |
| Total, w/o BPO | 233.21 | 234.03 | 233.20 | 233.20 |
| Work-Up | | | | |
| Methanol Washes | 3 | 3 | 3 | 3 |
| Soxhlet Solvent | Acetone | Acetone | Acetone | Acetone |
| Sieve Size (μm) | 300-600 | 300-600 | 300-600 | 300-600 |
| Modification | | | | |
| Amount of Polymer being modified, mL | N/A | N/A | N/A | N/A |
| Charged Water, mL | N/A | N/A | N/A | N/A |
| Ammonium Persulfate (AMPS), g | N/A | N/A | N/A | N/A |
| in Water for Addition, mL | N/A | N/A | N/A | N/A |
| NNNN-Tetramethylethylenediamine (TMED), g | N/A | N/A | N/A | N/A |
| in Water for Addition, mL | N/A | N/A | N/A | N/A |
| Vinylpyrrolidinone (VP), g | N/A | N/A | N/A | N/A |
| in Water for Addition, mL | N/A | N/A | N/A | N/A |

Example 19

Pore Structure Characterization

The pore structures of the adsorbent polymers were analyzed with either a Micromeritics AutoPore IV 9500 V1.09 a Mercury Penetrometer (Hg Intrusion instrument) or a Micromeritics ASAP 2010 instrument ($N_2$ Desorption). The results are shown in FIG. 1 where the pore volume is plotted as a function of the pore diameter. FIG. 1 is the log differential pore structures for Examples 1-18.

Example 20

Pore Structure Characterization

The pore volume is divided up into categories within pore size ranges for each of the sorbent polymers and these values are provided in Tables 7 and 8. In the first range, the capacity pore volume is that pore volume that is accessible to protein sorption and consists of the pore volume in pores larger than 100 Å in diameter. The effective pore volume is that pore volume that is selectively accessible to proteins smaller than approximately 50,000 Daltons and consists of pore diameters within the range of 100 to 1000 Å in diameter. The oversized pore volume is the pore volume accessible to proteins larger than approximately 50,000 Daltons and consists of the pore volume in pores larger than 1000 Å in diameter. The undersize pore volume is the pore volume in pores smaller than 100 Å diameter and is not accessible to proteins larger than about 10,000 Daltons.

In the second range, the capacity pore volume is that pore volume that is accessible to protein sorption and consists of the pore volume in pores larger than 1,000 Å in diameter. The effective pore volume is that pore volume that is selectively accessible to proteins smaller than about 300,000 Daltons and consists of pore diameters within the range of 1000 to 10000 Å in diameter. The oversized pore volume is the pore volume accessible to proteins larger than 300,000 Daltons and consists of the pore volume in pores larger than 1000 Å in diameter. The undersize pore volume is the pore volume in pores smaller than 1,000 Å diameter and is not accessible to proteins larger than about 10,000 Daltons.

In the third range, the capacity pore volume is that pore volume that is accessible to protein sorption and consists of the pore volume in pores larger than 500 Å in diameter. The effective pore volume is that pore volume that is selectively accessible to proteins smaller than 1,000,000 Daltons and consists of pore diameters within the range of 10,000 to 40,000 Å in diameter. The oversized pore volume is the pore volume accessible to proteins larger than 1,000,000 Daltons and consists of the pore volume in pores larger than 40,000 Å in diameter. The undersize pore volume is the pore volume in pores smaller than 10,000 Å diameter and is not accessible to proteins larger than about 40,000 Daltons.

Table 7 provides the pore volumes and pore volume ratios for Examples 1-18.

TABLE 7

| Polymer Name | Pore Volume (cc/g) of pores, diameter range 50-40000 Å | Pore Volume (cc/g) of pores, diameter range 100-1000 Å | Pore Volume (cc/g) of pores, diameter range 1000-10000 Å | Pore Volume (cc/g) of pores, diameter range 10000-40000 Å |
|---|---|---|---|---|
| TDG-057-064 | 0.82 | 0.71 | 0.00 | 0.00 |
| TDG-071-167 | 1.75 | 0.80 | 0.78 | 0.05 |
| RJR-090-030 | 2.25 | 0.32 | 1.72 | 0.17 |
| TDG-057-118 | 2.54 | 0.88 | 1.26 | 0.32 |
| RJR-090-013 | 2.54 | 0.88 | 1.26 | 0.32 |
| RJR-090-014 | N/A | N/A | N/A | N/A |
| RJR-090-016 | 2.27 | 0.91 | 1.08 | 0.20 |
| RJR-090-023 | 0.95 | 0.10 | 0.81 | 0.02 |

TABLE 7-continued

| Polymer Name | Pore Volume (cc/g) of pores, diameter range 50-40000 Å | Pore Volume (cc/g) of pores, diameter range 100-1000 Å | Pore Volume (cc/g) of pores, diameter range 1000-10000 Å | Pore Volume (cc/g) of pores, diameter range 10000-40000 Å |
|---|---|---|---|---|
| RJR-090-087 | 1.69 | 0.20 | 1.38 | 0.06 |
| RJR-090-091 | 1.46 | 0.25 | 1.20 | 0.01 |
| RJR-090-136 | 1.68 | 0.41 | 1.18 | 0.07 |
| RJR-090-137 | 1.91 | 0.24 | 1.53 | 0.10 |
| RT-075-14-1 | N/A | N/A | N/A | N/A |
| TDG-057-145 | 1.75 | 0.80 | 0.78 | 0.05 |
| RJR-090-178 | 1.36 | 0.15 | 1.12 | 0.05 |
| RJR-090-021 | 1.52 | 0.04 | 0.21 | 1.24 |
| RJR-090-187 | 0.88 | 0.05 | 0.13 | 0.68 |
| RJR-090-031 | 1.22 | 0.09 | 0.52 | 0.57 |

Table 8 provides the pore volume ratios for Examples 1-18.

TABLE 8

| Polymer Name | Ratio of Pore Volume Between 50-4000 Å 0 to pore volume between 100-1000 Å | Ratio of Pore Volume Between 50-40000 Å to pore volume between 1000-10000 Å | Ratio of Pore Volume Between 50-40000 Å to pore volume between 10000-40000 Å |
|---|---|---|---|
| TDG-057-064 | 1.2:1 | 219.8:1 | N/A |
| TDG-071-167 | 2.2:1 | 2.2:1 | 2.2:1 |
| RJR-090-030 | 6.9:1 | 1.3:1 | 13.4:1 |
| TDG-057-118 | 2.9:1 | 2.0:1 | 8.0:1 |
| RJR-090-013 | 2.9:1 | 2.0:1 | 8.0:1 |
| RJR-090-014 | N/A | N/A | N/A |
| RJR-090-016 | 2.5:1 | 2.1:1 | 11.4:1 |
| RJR-090-023 | 9.1:1 | 1.2:1 | 52.9:1 |
| RJR-090-087 | 8.4:1 | 1.2:1 | 27.2:1 |
| RJR-090-091 | 6.0:1 | 1.2:1 | 163.1:1 |
| RJR-090-136 | 4.1:1 | 1.4:1 | 25.7:1 |
| RJR-090-137 | 7.9:1 | 1.3:1 | 19.2:1 |
| RT-075-14-1 | N/A | N/A | N/A |
| TDG-057-145 | 2.2:1 | 2.2:1 | 37.6:1 |
| RJR-090-178 | 9.0:1 | 1.2:1 | 25.6:1 |
| RJR-090-021 | 42.1:1 | 7.1:1 | 1.2:1 |
| RJR-090-187 | 19.4:1 | 6.7:1 | 1.3:1 |
| RJR-090-031 | 13.9:1 | 2.3:1 | 2.1:1 |

Example 21

In Vitro *C. difficile* Toxin A(rTcdA)

The main objective of this study was to evaluate the ability of polymer beads (Porous beads ID's: TDG-057-118, RJR-090-136, RJR-090-091, RJR-090-137, RJR-090-023 and RJR-090-178, and non-porous bead ID: RT-075-1-14) to bind *Clostridium difficile* rTcdA. Eight types of beads, those with and without pores, were utilized. rTcdA was evaluated at a concentration of 100 µg/ml. No beads, and 20 µL of each non-porous and beads with pores were incubated with 100 (ideally 64.65) µg/ml of rTcdA at a 0.3 ml final working volume containing phosphate buffer saline in a 2-mL screw cap tube. Immediately after addition of toxins, one tube in each group containing no beads, beads without pores or porous beads stood for 0.583 h, allowing the beads to settle. A 225 µl sample was taken from these tubes. These were designated as the 0.583 h samples. Tubes from which the 1.5 and 2.5 h samples were taken were placed on a tube roller. A 225 µl sample was removed from these tubes. All samples were stored at −20° C. until use. Following collection of all samples, the protein concentration remaining in each sample was evaluated using the BCA (bicinchoninic acid) protein assay (Thermo Scientific, Cat. NO. 23225). Results are shown below. Beads TDG 057-118 demonstrated the best toxin removal, as well as RJR-090-136.

Table 9 provides the weight of polymers used for Example 21.

TABLE 9

| Sample Name | Amount (µL) | Bulk Wet Bead Density (mg/µL) | Weight (mg) |
|---|---|---|---|
| RJR-090-023 | 20 | 0.2794 | 5.6 |
| RJR-090-091 | 20 | 0.3863 | 7.7 |
| RJR-090-136 | 20 | 0.3240 | 6.5 |
| RJR-090-137 | 20 | 0.2794 | 5.6 |
| RJR-090-178 | 20 | 0.3487 | 7.0 |
| TDG-057-118 | 20 | 0.2239 | 4.5 |
| RT-075-14-1 | 20 | 0.8037 | 16.1 |

The *C. difficile* Toxin A adsorption results are shown in table 10

TABLE 10

| Expected | | Concentration (µg/mL) at Designated Time Point (h) | | | | | | | |
|---|---|---|---|---|---|---|---|---|---|
| Conc. | | BCA | | | | % Toxin Removal | | | |
| (µg/mL) | Sample | 0.00 h | 0.58 h | 1.50 h | 2.50 h | 0 h | 0.583 h | 1.5 h | 2.5 h |
| 100 | No Bead | 64.65 | 83.46 | 70.53 | 73.29 | 0% | 0% | 0% | 0% |
| | RT-075-14-1 | 64.65 | 70.54 | 61.14 | 69.76 | 0% | 0% | 5% | 0% |
| | TDG-057-118 | 64.65 | 63.14 | 20.55 | 14.05 | 0% | 2% | 68% | 78% |
| | RJR-090-136 | 64.65 | 62.89 | 18.54 | 16.36 | 0% | 3% | 71% | 75% |
| | RJR-090-091 | 64.65 | 67.21 | 31.72 | 16.41 | 0% | 0% | 51% | 75% |

TABLE 10-continued

| Expected | | Concentration (μg/mL) at Designated Time Point (h) | | | | | | | |
|---|---|---|---|---|---|---|---|---|---|
| Conc. | | BCA | | | | % Toxin Removal | | | |
| (μg/mL) | Sample | 0.00 h | 0.58 h | 1.50 h | 2.50 h | 0 h | 0.583 h | 1.5 h | 2.5 h |
| | RJR-090-137 | 64.65 | 74.87 | 32.68 | 16.68 | 0% | 0% | 49% | 74% |
| | RJR-090-023 | 64.65 | 67.49 | 27.03 | 18.7 | 0% | 0% | 58% | 71% |
| | RJR-090-178 | 64.65 | 70.06 | 21.88 | 15.63 | 0% | 0% | 66% | 76% |

Figure 2:
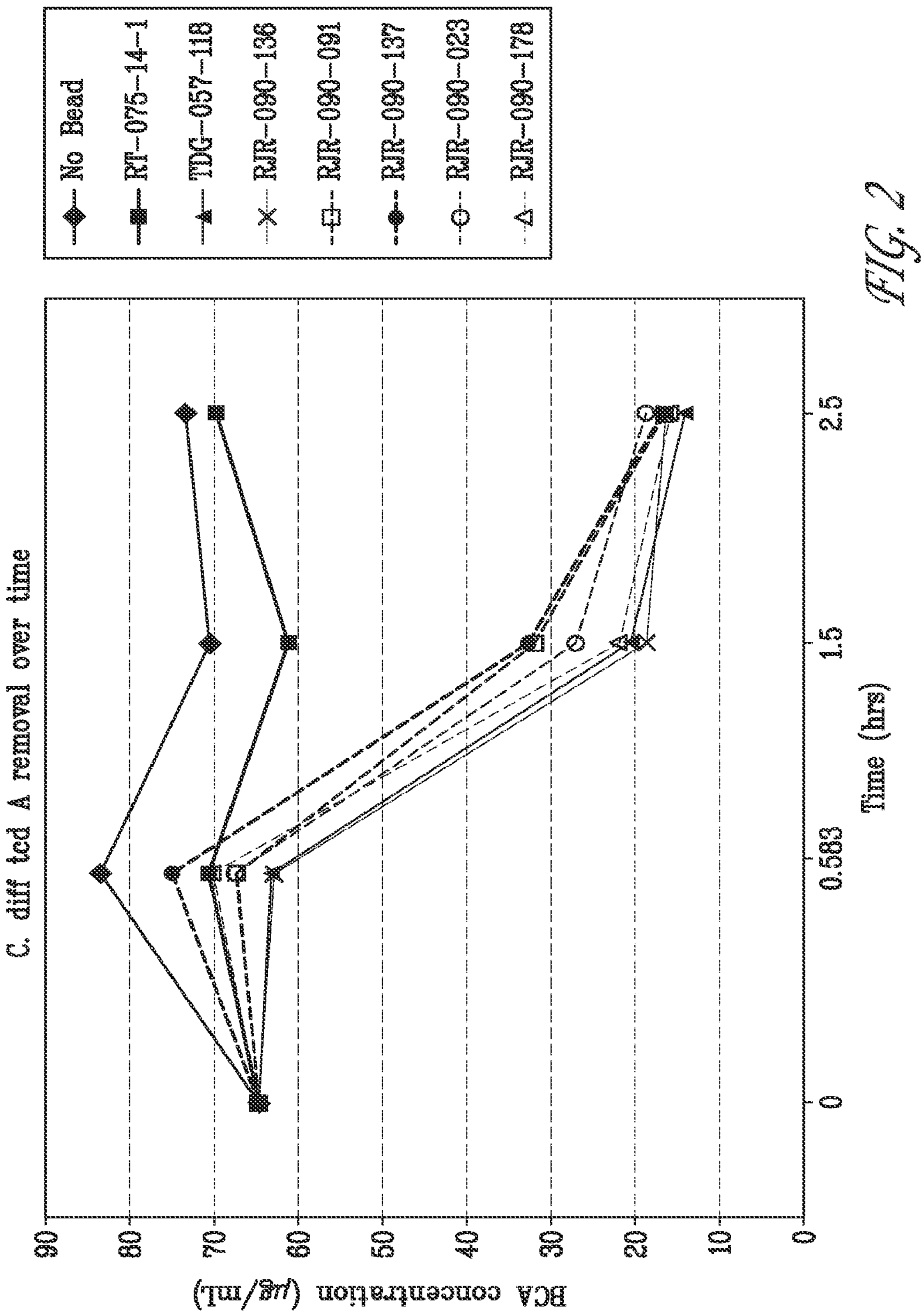
FIG. 2 illustrates the *Clostridium difficile* Toxin A removal as a function of time.

FIG. 2 shows *C. difficile* Toxin A removal over time.

Example 22

In Vitro *C. difficile* Toxin B (rTcdB)

The main objective of this study was to evaluate the ability of polymer beads (Porous bead ID: RJR-090-016, and non-porous bead ID: RJR-090-014) to bind and remove *Clostridium difficile* rTcdB toxin in vitro at toxin concentrations of 25 and 100 μg/mL, as compared to a no-bead control. In brief, either no beads, or a fixed volume (46 μL each) of either non-porous (≈37.0 μg dry bead weight) or porous beads (≈12.1 μg dry bead weight) were incubated with either 25 or 100 μg/ml of rTcdB in phosphate buffered saline at a 0.3 ml final working volume in a 2-mL screw cap microfuge tube. The experiment was performed to keep the interstitial volume (outside of the beads) constant at 0.3 mL. The weight of the porous beads reflects their high degree of porosity compared to the non-porous beads Immediately after addition of toxin, one tube in each group containing either no beads, non-porous bead or porous beads was allowed to sit without agitation for 45 minutes to allow the beads to settle by gravity. A 225 μl sample was taken from these tubes and stored at −20° C. These were designated as the 0.75 h samples. Sample tubes, designated 1.75 h and 2.75 h respectively, were mixed continuously on a tube roller. At time-points of 1.0 and 2.0 hours after the start of the experiment, respectively, tubes were removed from the roller and set in a rack for 45 min for the beads to settle. A 225 μl sample was removed from these tubes. All samples were stored at −20° C. until use. Following collection of all samples, the protein concentration remaining in each sample was evaluated using the BCA (bicinchoninic acid) protein assay (Thermo Scientific, Cat. NO. 23225). The results shown below in Table 11 represent the concentration of rTcdB toxin in each of the aliquoted samples, over time. Although non-porous beads demonstrate some binding to the toxin, the contribution of the porous bead is clear, particularly at higher concentrations, where saturation of the non-porous beads is evident, but is not observed in the porous beads.

The *C. difficile* Toxin B adsorption results are shown in Table 11.

TABLE 11

| Starting Concentration | | Concentration (μg/mL) at Designated Time Point (h) | | | % Removal |
|---|---|---|---|---|---|
| (μg/mL) | Sample | 0.75 | 1.75 | 2.75 | (at $T_{2.75\ h}$) |
| 25 | No Bead | 25.2 | 25.5 | 32.7 | ~0% |
| | Non-Porous Bead | 13.7 | 5.3 | 7.8 | 69% |
| | Porous Bead | 16.3 | Not Detected | 0.8 | 97% |

TABLE 11-continued

| Starting Concentration | | Concentration (μg/mL) at Designated Time Point (h) | | | % Removal |
|---|---|---|---|---|---|
| (μg/mL) | Sample | 0.75 | 1.75 | 2.75 | (at $T_{2.75\ h}$) |
| 100 | No Bead | 110.4 | 128.3 | 105.9 | 0% |
| | Non-Porous Bead | 118.5 | 92.5 | 94.2 | 6% |
| | Porous Bead | 90.9 | 8.4 | 2.3 | 98% |

Example 23

In Vitro *C. difficile* Toxin B (rTcdB)

The main objective of this study was to evaluate the ability of Cytosorbents' Beads (Porous beads ID's: TDG-057-118, RJR-090-136, RJR-090-091, RJR-090-137, RJR-090-023 and RJR-090-087, and non-porous bead ID: RT-075-1-14) to bind *Clostridium difficile* rTcdB. Seven types of beads, those with and without pores, and a no bead control were utilized. rTcdB was evaluated at a concentration of 100 μg/ml. No beads, and 20 μL (dry weight of sample, see table 11 below) of each non-porous and beads with pores were incubated with 100 (ideally 99.76) μg/ml of rTcdB at a 0.3 ml final working volume containing phosphate buffer saline in a 2-mL screw cap tube.

The weight of polymers used for Example 19 is shown in Table 12.

TABLE 12

| Sample Name | Amount (μL) | Bulk Wet Bead Density (mg/μL) | Weight (mg) |
|---|---|---|---|
| RJR-090-023 | 20 | 0.2794 | 5.6 |
| RJR-090-087 | 20 | 0.3487 | 7.0 |
| RJR-090-091 | 20 | 0.3863 | 7.7 |
| RJR-090-136 | 20 | 0.3240 | 6.5 |
| RJR-090-137 | 20 | 0.2794 | 5.6 |
| TDG-057-118 | 20 | 0.2239 | 4.5 |
| RT-075-14-1 | 20 | 0.8037 | 16.1 |

Immediately after addition of toxins, one tube in each group containing no beads, bead without pores or porous beads were stood for 0.583 h, allowing the beads to settle. A 225 μl sample was taken from these tubes. These were designated as the 0.583 h samples. Tubes from which the 1.5 and 2.5 h samples were taken were placed on a tube roller. A 225 μl sample was removed from these tubes. All samples were stored at −20° C. until use. Following collection of all samples, the protein concentration remaining in each sample was evaluated using the BCA (bicinchoninic acid) protein assay (Thermo Scientific, Cat. NO. 23225). Results are shown below. Beads RJR-090-136 demonstrated the best toxin removal, followed by TDG 057-118 and/or RJR 090-137.

The *C. difficile* Toxin B adsorption results are shown in Table 13.

TABLE 13

| *C. diff* toxin B Expected Conc. | | Concentration (μg/mL) at Designated Time Point (h) BCA | | | | % of Toxin Removal | | | |
|---|---|---|---|---|---|---|---|---|---|
| (μg/mL) | Sample | 0 h | .583 h | 1.5 h | 2.5 h | 0 h | .583 h | 1.5 h | 2.5 h |
| 100 | No Bead | 99.76 | 83.53 | 81.94 | 71.96 | 0% | 16% | 18% | 28% |
| | RT-075-14-1 | 99.76 | 122.14 | 81.58 | 93.07 | 0% | 0% | 18% | 7% |
| | TDG-057-118 | 99.76 | 91.18 | 39.28 | 21.05 | 0% | 9% | 61% | 79% |
| | RJR-090-136 | 99.76 | 82.83 | 36.43 | 17.81 | 0% | 17% | 63% | 82% |
| | RJR-090-091 | 99.76 | 93.73 | 62.79 | 30.58 | 0% | 6% | 37% | 69% |
| | RJR-090-137 | 99.76 | 85.28 | 52.45 | 19 | 0% | 15% | 47% | 81% |
| | RJR-090-023 | 99.76 | 71.52 | 61.08 | 38.05 | 0% | 28% | 39% | 62% |
| | RJR-090-087 | 99.76 | 92.92 | 59.15 | 23.11 | 0% | 7% | 41% | 77% |

Figure 3:
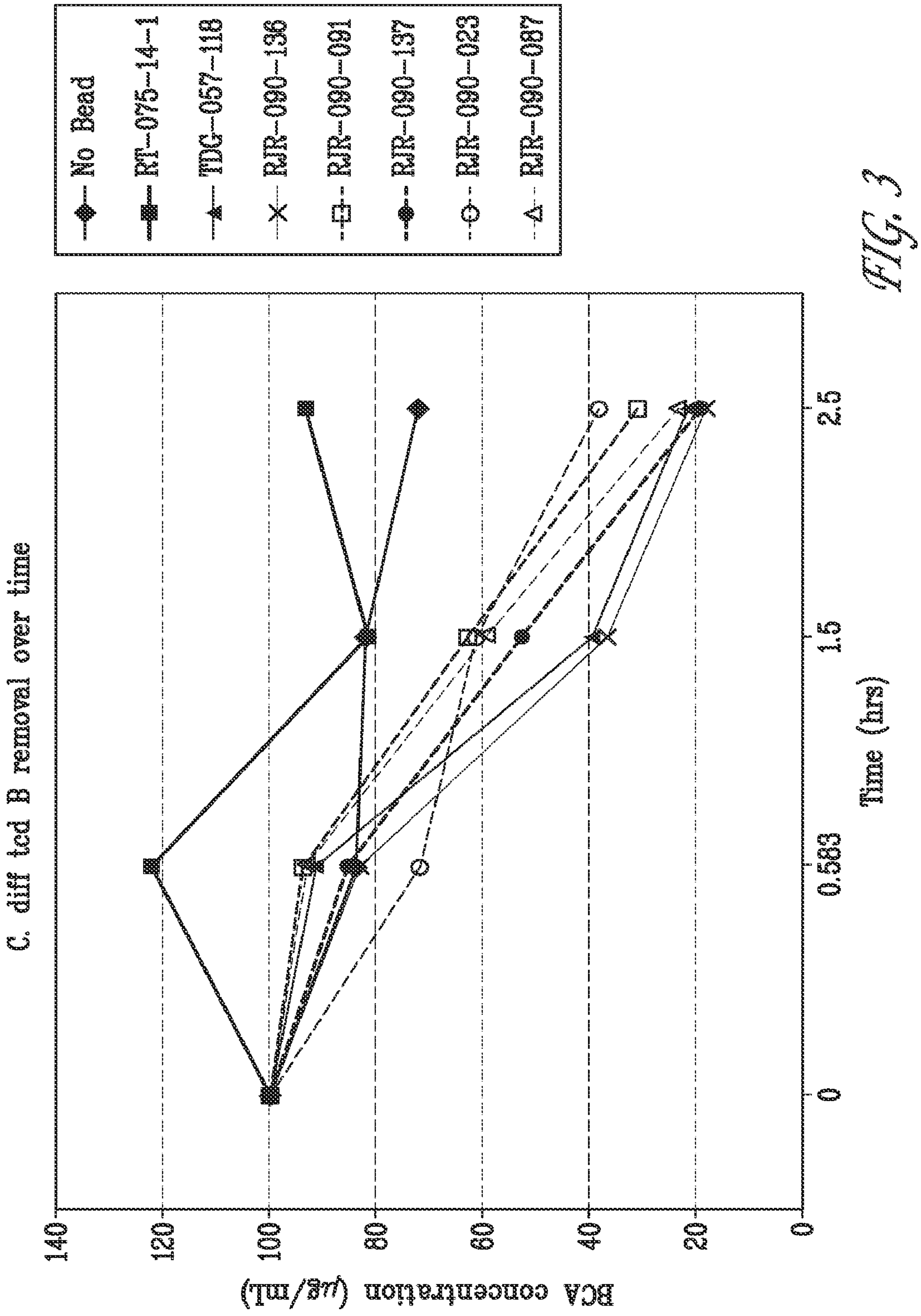
FIG. 3 illustrates the *Clostridium difficile* Toxin B removal as a function of time.

FIG. 3 shows *C. difficile* Toxin B removal over time.

Example 24

In Vitro Botulinum Neurotoxin Type A1 (BoNT/A1) Study

The main objective of this study was to evaluate the ability of polymer beads (Porous bead ID: TDG-057-118, and non-porous bead ID: RT-075-14-1). Two types of beads, those with and without pores, were utilized. BoNT/A1 was evaluated at concentrations of 10, 50 and 100 μg/ml in phosphate buffered saline. No beads, or a fixed volume of 40 μL each of either non-porous (≈32.1 μg dry bead weight) or porous beads (≈5.5 μg dry bead weight) were incubated with either 10, 50 or 100 μg/ml of BoNT/A1 at a 0.3 ml final working volume in a 2-mL screw cap microfuge tube. The experiment was performed to keep the interstitial volume (outside of the beads) constant at 0.3 mL. The weight of the porous beads reflects their high degree of porosity compared to the non-porous beads. Immediately after addition of BoNT/A1, a 225 μl sample was taken from one tube in each group containing no beads, non-porous beads, or porous beads and stored at −20° C. These were designated as the 0 h samples. Tubes correlating to the 1 and 2 h samples were placed on a tube roller and mixed continuously. After incubation at room temperature of either 1 or 2 hours, a 225 μl sample was removed from the appropriate tubes. All samples were stored at −20° C. until use. Following collection of all samples, the protein concentration remaining in each sample was evaluated using the BCA (bicinchoninic acid) protein assay (Thermo Scientific, Cat. NO. 23225). As can be seen in the results listed in Table 14, at concentrations up to 100 μg/mL, the porous beads removed more than 95% of the BoNT/A1 toxin, compared to either the no-bead control or the non-porous beads.

The Botulinum Neurotoxin Type A1 adsorption results are shown in Table 14.

TABLE 14

| Starting Concentration (μg/mL) | Sample | Concentration (μg/mL) at Designated Time Point (h) 0 h | 1 h | 2 h | % Removal (at $T_{2\ h}$) |
|---|---|---|---|---|---|
| 10 | No Bead | 10.2 | 6.9 | 7.2 | 29% |
| | Non-Porous Bead | 10.2 | 7.4 | 5.6 | 45% |
| | Porous Bead | 7.2 | Not Detected | Not Detected | 100% |

TABLE 14-continued

| Starting Concentration (μg/mL) | Sample | Concentration (μg/mL) at Designated Time Point (h) 0 h | 1 h | 2 h | % Removal (at $T_{2\ h}$) |
|---|---|---|---|---|---|
| 50 | No Bead | 43.4 | 47.2 | 42.8 | 1% |
| | Non-Porous Bead | 47.3 | 43.7 | 38.6 | 18% |
| | Porous Bead | 37.9 | 1.7 | 1.5 | 96% |
| 100 | No Bead | 117.6 | 96.8 | 105.8 | 10% |
| | Non-Porous Bead | 94.1 | 120.3 | 105.8 | 0% |
| | Porous Bead | 74.6 | 4.5 | 3.5 | 95% |

Example 25

In Vitro Shiga Like Toxin 1 Study

The main objective of this study was to evaluate the ability of CytoSorbents polymer beads (Porous bead ID: TDG-071-167, Large Pore Bead ID: RJR-090-013 and non-porous bead ID: RT-075-14-1) to bind Shiga Like Toxin 1. Three types of beads, those with and without pores, were utilized. Shiga Like Toxin 1 was evaluated at concentrations of 50 and 100 μg/ml in phosphate buffered saline. No beads, and 42 μL of porous (≈12.5 μg dry bead weight), 42 μL of large pore (≈9.5 μg dry bead weight) and 42 μL of non-porous beads (≈33.8 μg dry bead weight) were incubated with either 50 or 100 μg/ml of Shiga Like Toxin 1 at a 0.3 ml final working volume in a 2-mL screw cap microfuge tube.

Immediately after addition of Shiga Like Toxin 1, a 225 μl sample was taken from one tube in each groups containing no beads, non-porous beads, or porous beads and stored at −20° C. These were designated as the 0.25 h samples. Tubes correlating to the 1.25 and 2.25 h samples were placed on a tube roller and mixed continuously. After incubation at room temperature of either 1.25 or 2.25 hours, a 225 μl sample was removed from the appropriate tubes. All samples were stored at −20° C. until use. Following collection of all samples, the protein concentration remaining in each sample was evaluated using the BCA (bicinchoninic acid) protein assay (Thermo Scientific, Cat. NO. 23225). As can be seen, the both standard and large porous beads have a better kinetics of removal in contrast to the non-porous beads.

The Shiga Like Toxin 1 adsorption results are shown in Table 15.

TABLE 15

| Stx1 Starting Concentration (μg/ml) | Sample | Concentration (μg/ml) at Designated Time Point 0.25 h | 1.25 h | 2.25 h | % removal at T0.25 h | % removal at T2.25 h |
|---|---|---|---|---|---|---|
| 50 | No Bead Control | 36.4 | 23.46 | 27.77 | 27% | 44% |
| | RT-075-14-1 | 23.38 | 24.71 | 21.52 | 53% | 57% |
| | TDG-071-167 | 20.93 | Not Determined | 0.99 | 58% | 98% |
| | RJR-090-013 | 20.93 | Not Determined | 0.52 | 58% | 99% |
| 100 | No Bead Control | 53.58 | 42.23 | 47.78 | 46% | 52% |
| | RT-075-14-1 | 41.51 | 37.6 | 49.65 | 58% | 50% |
| | TDG-071-167 | 39.55 | 3.7 | 0.8 | 60% | 99% |
| | RJR-090-013 | 38.74 | Not Determined | 0.71 | 61% | 99% |

Example 26

In Vitro Shiga Like Toxin 2 Study

The main objective of this study was to evaluate the ability of CytoSorbents polymer beads (Porous bead ID: TDG-071-167, Large Pore Bead ID: RJR-090-013 and non-porous bead ID: RT-075-14-1) to bind Shiga Like Toxin 2. Three types of beads, those with and without pores, were utilized. Shiga Like Toxin 2 was evaluated at concentrations of 50 and 100 μg/ml in phosphate buffered saline. No beads, and 42 μL of porous (≈12.5 μg dry bead weight), 42 μL of large pore (≈9.5 μg dry bead weight) and 42 μL of non-porous beads (≈33.8 μg dry bead weight) were incubated with either 50 or 100 μg/ml of Shiga Like Toxin 2 at a 0.3 ml final working volume in a 2-mL screw cap microfuge tube Immediately after addition of Shiga Like Toxin 2, a 225 μl sample was taken from one tube in each groups containing no beads, non-porous beads, or porous beads and stored at −20° C. These were designated as the 0.25 h samples. Tubes correlating to the 1.25 and 2.25 h samples were placed on a tube roller and mixed continuously. After incubation at room temperature of either 1.25 or 2.25 hours, a 225 μl sample was removed from the appropriate tubes. All samples were stored at −20° C. until use. Following collection of all samples, the protein concentration remaining in each sample was evaluated using the BCA (bicinchoninic acid) protein assay. As can be seen, the both standard and large porous beads have a better kinetics of removal in contrast to the non-porous beads.

The Shiga Like Toxin 2 adsorption results are shown in Table 16.

TABLE 16

| Stx2 Starting Concentration (μg/ml) | Sample | Concentration (μg/ml) at Designated Time Point 0.25 h | 1.25 h | 2.25 h | % removal at T0.25 h | % removal at T2.25 h |
|---|---|---|---|---|---|---|
| 50 | No Bead Control | 35.22 | 35.63 | 32.86 | 30% | 34% |
| | RT-075-14-1 | 32 | 30.57 | 31.32 | 36% | 37% |
| | TDG-071-167 | 22.45 | 0.54 | 1.9 | 55% | 96% |
| | RJR-090-013 | 27.75 | 1.03 | 0.95 | 45% | 98% |
| 100 | No Bead Control | 69.4 | 70.02 | 69.03 | 31% | 31% |
| | RT-075-14-1 | 60.51 | 65.58 | 55.75 | 39% | 44% |
| | TDG-071-167 | 59.24 | 4.33 | 2.1 | 41% | 98% |
| | RJR-090-013 | 54.8 | 2.38 | 1.06 | 45% | 99% |

Example 27

In Vitro Ricin Toxin Study

The main objective of this study was to evaluate the ability of CytoSorbents polymer beads (Small Porous bead ID: TDG-057-145, Modified, Batch 1, −106/+45, Large porous bead ID: RJR-090-016 and non-porous bead ID: RJR-090-014) to bind ricin toxin. Three types of beads, those with and without pores, were utilized. Ricin toxin was evaluated at concentrations of 100 and 1000 μg/ml in phosphate buffered saline. No beads, and 43 μL of porous beads (≈14.6 μg dry bead weight), 43 μL of large pore (≈11.3 μg dry bead weight), and 44 μL of non-porous beads (≈35.4 μg dry bead weight) were incubated with either 100 or 1000 μg/ml of ricin toxin at a 0.3 ml final working volume in a 2-mL screw cap microfuge tube. Immediately after addition of ricin toxin, a 225 μl sample was taken from one tube in each groups containing no beads, non-porous beads, or porous beads and stored at −20° C. These were designated as the 0.75 h samples. Tubes correlating to the 1.75 and 2.75 h samples were placed on a tube roller and mixed continuously. After incubation at room temperature of either 1.75 or 2.75 hours, a 225 μl sample was removed from the appropriate tubes. All samples were stored at −20° C. until use. Following collection of all samples, the protein concentration remaining in each sample was evaluated using the BCA (bicinchoninic acid) protein assay (Thermo Scientific, Cat. NO. 23225). As can be seen, the small porous beads have a better kinetics of removal in contrast to the large porous beads initially. No-bead control or the non-porous beads removed no toxins and no more than 9%, respectively.

The Ricin Toxin adsorption results are shown in Table 17.

TABLE 17

| Ricin Toxin Starting Concentration | | Concentration (μg/ml) at Designated Time Point | | | % removal | % removal |
|---|---|---|---|---|---|---|
| (μg/ml) | Sample | 0.75 h | 1.75 h | 2.75 h | at T0.75 h | at T2.75 h |
| 100 | No Bead Control | 111.21 | 114.2 | 117.69 | 0% | 0% |
| | RJR-090-014 | 90.8 | 104.36 | 109.02 | 9% | 0% |
| | TDG-057-145 | 2.67 | 2.05 | 2.38 | 97% | 98% |
| | RJR-090-016 | 12.77 | 1.28 | 0.62 | 87% | 99% |
| 1000 | No Bead Control | 1136.33 | 1246.77 | 1025.9 | 0% | 0% |
| | RJR-090-014 | 1240.62 | 1217.81 | 1341.14 | 0% | 0% |
| | TDG-057-145 | 170.4 | 8.7 | 10.49 | 83% | 99% |
| | RJR-090-016 | 353.44 | 11.98 | 9.18 | 65% | 99% |

Example 28

In Vitro Cholera Toxin Study

The main objective of this study was to evaluate the ability of CytoSorbents™ polymer beads (Small Porous bead ID: TDG-057-145, Modified, Batch 1, −106/+45, Large porous beads bead ID: RJR-090-016 and non-porous bead ID: RJR-090-014) to bind cholera toxin. Three types of beads, those with and without pores, were utilized. Cholera toxin was evaluated at concentrations of 50 and 100 μg/ml in phosphate buffered saline. No beads, and 43 μL of standard porous beads (≈14.6 μg dry bead weight), 43 μL of large pore (≈11.3 μg dry bead weight), and 44 μL of non-porous beads (≈35.4 μg dry bead weight) were incubated with either 50 or 100 μg/ml of cholera toxin at a 0.3 ml final working volume in a 2-mL screw cap micro fuge tube. Immediately after addition of cholera toxin, a 225 μl sample was taken from one tube in each groups containing no beads, non-porous beads, or porous beads and stored at −20° C. These were designated as the 0.75 h samples. Tubes correlating to the 1.75 and 2.75 h samples were placed on a tube roller and mixed continuously. After incubation at room temperature of either 1.75 or 2.75 hours, a 225 μl sample was removed from the appropriate tubes. All samples were stored at −20° C. until use. Following collection of all samples, the protein concentration remaining in each sample was evaluated using the BCA (bicinchoninic acid) protein assay (Thermo Scientific, Cat. NO. 23225). As can be seen, the small porous beads have a better kinetics of removal in contrast to the large porous beads. No-bead control or the non-porous beads removed no toxins and less than 25%, respectively.

The cholera toxin adsorption results are shown Table 18.

TABLE 18

| Starting Concentration | | Concentration (μg/mL) at Designated Time Point (h) | | | % Removal | % Removal |
|---|---|---|---|---|---|---|
| (μg/mL) | Sample | 0.75 | 1.75 | 2.75 | (at $T_{0.75\ h}$) | (at $T_{2.75\ h}$) |
| 50 | No Bead Control | 63.82 | 57.29 | 65.16 | 0% | 0% |
| | RJR-090-014 | 38.54 | 37.24 | 38.55 | 23% | 23% |
| | TDG-057-145 | 4.37 | 3.24 | 2.41 | 91% | 95% |
| | RJR-090-016 | 6.38 | 3.24 | 3.41 | 87% | 93% |
| 100 | No Bead Control | 96.06 | 128.22 | 113.45 | 4% | 0% |
| | RJR-090-014 | 76.13 | 91.23 | 79.42 | 24% | 21% |
| | TDG-057-145 | 5.94 | 4.91 | 3.24 | 94% | 97% |
| | RJR-090-016 | 10.64 | 4.1 | 2.35 | 89% | 98% |

Example 29

In Vitro *C. perfringens* Enterotoxin Study

The main objective of this study was to evaluate the ability of CytoSorbents polymer beads (Porous bead ID: TDG-071-167, Large Pore Bead ID: TDG-057-118 and non-porous bead ID: RT-075-14-1) to bind *C. perfringens* enterotoxin. Three types of beads, those with and without pores, were utilized. *C. perfringens* enterotoxin was evaluated at concentrations of 50 and 100 (ideally 11.46 and 31.42) μg/ml in phosphate buffered saline. No beads, and 40 μL of porous beads (≈11.9 μg dry bead weight), 40 μL of large pore (≈9.0 μg dry bead weight) and 40 μL of non-porous beads (≈32.1 μg dry bead weight) were incubated with either 50 or 100 (ideally 11.46 and 31.42) μg/ml of *C. perfringens* enterotoxin at a 0.3 ml final working volume in a 2-mL screw cap microfuge tube. Immediately after addition of *C. perfringens* enterotoxin, a 225 μl sample was taken from one tube in each groups containing no beads, non-porous beads, or porous beads and stored at −20° C. These were designated as the 0.5 h samples. Tubes correlating to the 1.5 and 2.5 h samples were placed on a tube roller and mixed continuously. After incubation at room temperature of either 1.5 or 2.5 hours, a 225 μl sample was removed from the appropriate tubes. All samples were stored at −20° C. until use. Following collection of all samples, the protein concentration remaining in each sample was evaluated using the BCA (bicinchoninic acid) protein assay (Thermo Scientific, Cat. NO. 23225). As can be seen, the large porous beads have a better kinetics of removal from 31.42 mg/mL of toxin in contrast to the standard and non-porous beads. No-bead control or the non-porous beads did not remove any toxin.

The *C. perfringens* Enterotoxin adsorption results are shown in Table 19.

TABLE 19

| *C. perfringens* Enterotoxin Expected Concentration (μg/ml) | Sample | Concentration (μg/ml) at Designated Time Point BCA 0 h | 0.5 h | 1.5 h | 2.5 h | % removal at T0.5 h | % removal at T2.5 h |
|---|---|---|---|---|---|---|---|
| 50 | No Bead | 11.46 | 18.05 | 13.94 | 15.43 | 0% | 0% |
| | RT-075-14-1 | — | 12.4 | 11.82 | 17.59 | 0% | 0% |
| | TDG-071-167 | — | 4.22 | 0.35 | 2.63 | 63% | 77% |
| | TDG-057-118 | — | 7.81 | 0.98 | 1.74 | 32% | 85% |
| 100 | No Bead | 31.42 | 34.91 | 34.73 | 34.78 | 0% | 0% |
| | RT-075-14-1 | — | 36.25 | 35.82 | 37.31 | 0% | 0% |
| | TDG-071-167 | — | 27.73 | 0.54 | 2.82 | 12% | 91% |
| | TDG-057-118 | — | 19.52 | 0.52 | 2.25 | 38% | 93% |

Example 30

In Vitro *Staphylococcus* Enterotoxin B Study

The main objective of this study was to evaluate the ability of CytoSorbents polymer beads (Small Porous bead ID: TDG-057-145, and non-porous bead ID: RJR-090-014) to bind *Staphylococcus* enterotoxin B. Two types of beads, those with and without pores, were utilized. *Staphylococcus* enterotoxin B was evaluated at concentrations of 50 and 100 (ideally 43.02 and 97.85) μg/ml in phosphate buffered saline. No beads, and 43 μL of porous (≈14.6 μg dry weight) and 44 μL of non-porous beads (≈35.4 μg dry weight) were incubated with either 50 or 100 (ideally 43.02 and 97.85)μg/ml of *Staphylococcus* enterotoxin at a 0.3 ml final working volume in a 2-mL screw cap microfuge tube. Immediately after addition of *Staphylococcus* enterotoxin, a 225 μL sample was taken from one tube in each groups containing no beads, non-porous beads, or porous beads and stored at −20° C. These were designated as the 0.75 h samples. Tubes correlating to the 1.75 and 2.75 h samples were placed on a tube roller and mixed continuously. After incubation at room temperature of either 1.75 or 2.75 hours, a 225 μL sample was removed from the appropriate tubes. All samples were stored at −20° C. until use. Following collection of all samples, the protein concentration remaining in each sample was evaluated using the BCA (bicinchoninic acid) protein assay. As can be seen, the small porous beads have a better kinetics of removal (greater than or equal to 98% by 0.75 h) in contrast to the non-porous beads. No-bead control or the non-porous beads did not remove toxins as efficiently.

The *Staphylococcus* Enterotoxin B adsorption results are shown in Table 20.

TABLE 20

| *Staph* Enterotoxin Starting Concentration (μg/ml) | Sample | Concentration (μg/ml) at Designated Time Point 0.75 h | 1.75 h | 2.75 h | % removal at T0.75 h | % removal at T2.75 h |
|---|---|---|---|---|---|---|
| 50 | No Bead Control | 43.02 | 59.09 | 42.13 | 14% | 16% |
| | RJR-090-014 | 31 | 38.04 | 23.38 | 38% | 53% |
| | TDG-057-145 | 1.24 | 1.36 | ND | 98% | 100% |
| 100 | No Bead Control | 97.85 | 100.3 | 95.43 | 2% | 5% |
| | RJR-090-014 | 54.08 | 72.36 | 70.8 | 46% | 29% |
| | TDG-057-145 | 1.77 | 1.99 | 0.92 | 98% | 99% |

Example 31

In Vitro *Staphylococcus aureus* α-Hemolysin

Example 31: In Vitro *Staphylococcus aureus* α-Hemolysin

The main objective of this study was to evaluate the ability of two different CytoSorbents porous bead types (Small Pore: RJR-100-144; Large Pore: RJR-100-168) and non-porous beads (RJR-090-158) to bind *Staphylococcus aureus* α-Hemolysin. *S. aureus* α-Hemolysin was evaluated at concentrations of 50 and 100 μg/ml in phosphate buffered saline. No beads, and 40 μL of porous beads (≈11.9 μg dry bead weight), 40 μL of large pore (≈9.0 μg dry bead weight), and 40 μL of non-porous beads (≈32.1 μg dry bead weight) were incubated with either 50 or 100 μg/ml of toxin at a 0.3 ml final working volume in a 1.5-mL screw cap tube. Immediately after addition of *Staphylococcus aureus* α-Hemolysin enterotoxin, a 225 μl sample was taken from one tube in each group containing no beads, non-porous beads, or porous beads and immediately stored at −20° C. Tubes correlating to the 0.5 h, 1.5 h, and 2.5 hours samples were placed on a tube roller and mixed continuously. After incubation at room temperature of either 0.5 h, 1.5 h, or 2.5 hours, a 225 μl sample was removed from the appropriate tubes. All samples were stored at −20° C. until use. Following collection of all samples, the protein concentration remaining in each sample was evaluated using the BCA (bicinchoninic acid) protein assay (Thermo Scientific, Cat. NO. 23225). The BCA assay indicates that both porous polymers have better kinetics of removal than the no bead control and the non-porous beads.

*S. aureus* α-Hemolysin adsorption results via BCA protein assay and NanoDrop are shown in Table 21 below.

TABLE 21

| *Staphylococcus aureus* α-Hemolysin Expected Concentration (μg/ml) | Sample | Concentration (μg/mL) at Designated Time Point BCA 0 h | 0.5 h | 1.5 h | 2.5 h | % removal at T0.5 h | % removal at T2.5 h |
|---|---|---|---|---|---|---|---|
| 50 | No Bead (PBS) | 57.31 | 53.93 | 54.66 | 48.63 | 6% | 15% |
| | RJR-090-158 | | 47.14 | 54.66 | 49.5 | 18% | 14% |
| | RJR-100-144 | | 23.8 | 4.15 | 0 | 58% | 100% |
| | RJR-100-168 | | 42.47 | 0 | 0 | 26% | 100% |
| 100 | No Bead (PBS) | 119.96 | 113.44 | 91.62 | 108.89 | 5% | 9% |
| | RJR-090-158 | | 97.14 | 103.45 | 95.8 | 19% | 20% |
| | RJR-100-144 | | 39.45 | 16.44 | 3.28 | 67% | 97% |
| | RJR-100-168 | | 66.36 | 0 | 0 | 45% | 100% |

Example 32

In Vitro *Escherichia Coli* STa Toxin

The main objective of this study was to evaluate the ability of various CytoSorbents porous bead types (bead #1: SFA-102-106, bead #2: CytoSorb Lot 08311, bead #3: TDG-057-118) and non-porous beads (RT-075-14-1) to bind *Escherichia coli* STa toxin. *Escherichia coli* STa toxin was evaluated at concentrations of 50 and 100 μg/mL in phosphate buffered saline. No beads, 40 μL of SFA-102-106 (≈9.0 μg dry bead weight), 40 μL of CytoSorb Lot 083111 (≈11.9 μg dry bead weight), 40 μL of TDG-057-118 (≈9.0 μg dry bead weight), and 40 μL of non-porous beads (≈32.1 μg dry bead weight) were incubated with either 50 or 100 μg/ml of *Escherichia coli* STa toxin at a 0.3 ml final working volume in a 1.5-mL screw cap tube. Immediately after addition of *Escherichia coli* STa toxin, a 225 μl sample was taken from one tube in each groups containing no beads, non-porous beads, or porous beads and immediately stored at −20° C. Tubes correlating to the 0.5 h, 1.5 h, and 2.5 hours samples were placed on a tube roller and mixed continuously. After incubation at room temperature of either 0.5 h, 1.5 h, or 2.5 hours, a 225 μl sample was removed from the appropriate tubes. All samples were stored at −20° C. until use. Following collection of all samples, the protein concentration remaining in each sample was evaluated using the BCA (bicinchoninic acid) protein assay (Thermo Scientific, Cat. NO. 23225) The BCA assay indicates that all three porous polymers have better kinetics of removal than the no bead control and the non-porous beads.

The *Escherichia coli* STa toxin adsorption results are shown in Table 22.

TABLE 22

| Expected Concentration (μg/mL) | Sample | Concentration (μg/ml) at Designated Time Point BCA 0 h | 0.5 h | 1.5 h | 2.5 h | % removal at T0.5 h | % removal at T2.5 h |
|---|---|---|---|---|---|---|---|
| 50 | No Bead | 71.72 | 58.24 | 55.54 | 55.55 | 19% | 23% |
| | RT-075-14-1 | — | 50.16 | 54.85 | 71.72 | 30% | 0% |
| | SFA-102-106 | — | 55.55 | 7.03 | 4.34 | 23% | 94% |
| | Standard-083111 | — | 58.24 | 8.73 | 1.64 | 19% | 98% |
| | TDG-057-118 | — | 55.55 | 4.33 | 1.05 | 58% | 99% |
| 100 | No Bead | 133.71 | 128.32 | 125.62 | 136.41 | 4% | 0% |
| | RT-075-14-1 | — | 131.01 | 128.32 | 133.71 | 2% | 0% |
| | SFA-102-106 | — | 106.75 | 9.72 | 4.34 | 20% | 97% |
| | Standard-083111 | — | 106.8 | 20.51 | 12.42 | 20% | 91% |
| | TDG-057-118 | — | 112.14 | 70.03 | 4.44 | 16% | 97% |

What is claimed:

1. A method of reducing contamination by one or more toxins in a biological substance, said method comprising:

a. contacting the biological substance with an effective amount of a sorbent capable of sorbing the toxin, wherein the sorbent comprises a plurality of pores ranging from 50 Å to 40,000 Å with a pore volume of 0.5 cc/g to 5.0 cc/g and a size of 0.05 mm to 2 cm, wherein the sorbent comprises a coated polymer comprising at least one crosslinking agent and wherein said toxins comprise endogenous toxins having a molecular weight of greater than 50,000 Daltons; and b. sorbing the toxin;

wherein the sorbent has:

(i) a ratio of pore volume between 50 Å to 40,000 Å (pore diameter) to pore volume between 100 Å to 1,000 Å (pore diameter) of the sorbent is smaller than 3:1; or (ii) a ratio of pore volume between 50 Å to 40,000 Å (pore diameter) to pore volume between 1,000 Å to 10,000 Å (pore diameter) of the sorbent is smaller than 2:1; or (iii) a ratio of pore volume between 50 Å to 40,000 Å (pore diameter) to pore volume between 10,000 Å to 40,000 Å (pore diameter) of the sorbent is smaller than 3:1; and wherein the toxin is an exotoxin produced by a microorganism that can comprise one or more bacteria, viruses, fungi or parasites; wherein said toxins comprise proteins, peptides, carbohydrates, lipids, nucleic acids, or combinations thereof.

2. The method of claim 1, wherein the sorbent is biocompatible.

3. The method of claim 1, wherein the polymer is a microporous polymeric sorbent.

4. The method of claim 1, wherein the sorbing occurs in vivo.

5. The method of claim 1, wherein the sorbing occurs ex vivo.

6. The method of claim 1, wherein the biological substance comprises cells or physiologic fluids such as saliva, nasopharyngeal fluid, blood, plasma, serum, saliva, gastrointestinal fluid, bile, cerebrospinal fluid, pericardial, vaginal fluid, seminal fluid, prostatic fluid, peritoneal fluid, pleural fluid, urine, synovial fluid, interstitial fluid, intracellular fluid, extracellular fluid, lymph, mucus, or vitreous humor.

7. The method of claim 1, wherein the method further comprises the steps of producing or purifying a blood product or biologic.

8. The method of claim 7, wherein the blood product comprises whole blood, packed red blood cells, platelets, plasma, cryoprecipitate, white blood cells, pluripotent stem cells, T-cells, B-cells, or other cells of myloid or lymphoid origin and their progenitors.

9. The method of claim 1, wherein contamination by the toxin is systemic or localized.

10. The method of claim 1, wherein the sorbent is introduced through a body cavity.

11. The method of claim 10, wherein the sorbent is introduced orally, vaginally, rectally or nasally, through a feeding tube or topically.

12. The method of claim 1, wherein the sorbent is introduced by hemoperfusion.

13. The method of claim 1, wherein the sorbent is used for extracorporeal treatment of a biological substance comprising saliva, blood, plasma, serum, gastrointestinal fluid, cerebrospinal fluid, vaginal fluid, peritoneal fluid, pleural fluid, urine, synovial fluid, lymph, alveolar mucus or vitreous humor.

14. The method of claim 1, wherein the sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 100 Å to 1,000 Å (pore diameter) of the sorbent is smaller than 3.1.

15. The method of claim 1, wherein the sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 1,000 Å to 10,000 Å (pore diameter) of the sorbent is smaller than 2:1.

16. The method of claim 15, wherein the toxin has a molecular weight in the range of from 50,000 Daltons to 450,000 Daltons.

17. The method of claim 1, wherein the sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 10,000 Å to 40,000 Å (pore diameter) of the sorbent is smaller than 3:1.

18. The method of claim 1, wherein the sorbent comprises a plurality of pores comprising at least one crosslinking agent, at least one monomer, and at least one dispersing agent.

19. The method of claim 18, wherein the dispersing agent is one or more of hydroxyethyl cellulose, hydroxypropyl cellulose, poly (hydroxyethyl methacrylate), poly (hydroxyethyl acrylate), poly (hydroxypropyl methacrylate), poly (hydroxypropyl acrylate), poly (dimethylaminoethyl methacrylate), poly (dimethylaminoethyl acrylate), poly (diethylaminoethyl methacrylate), poly (diethylaminoethyl acrylate), poly(vinyl alcohol), poly (N-vinylpyrrolidinone), salts of poly (methacrylic acid), or salts of poly(acrylic acid).

20. The method of claim 18, wherein the crosslinking agent is one or more of divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, or divinylformamide.

21. The method of claim 18, wherein monomer is one or more of divinylbenzene and ethylvinylbezene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythritol dimethacrylate, pentaerythritol trimethacrylate, pentaerythritol tetramethacrylate, pentaerythritol diacrylate, pentaerythritol triacrylate, pentaerythritol tetraacrylate, dipentaerythritol dimethacrylate, dipentaerythritol trimethacrylate, dipentaerythritol tetramethacrylate, dipentaerythritol diacrylate, dipentaerythritol triacrylate, dipentaerythritol tetraacrylate, divinylformamide and mixtures thereof.

22. The method of claim 1, wherein the sorbent is a mixture of sorbents with two or more different pore sizes.

23. The method of claim 1, wherein the sorbent is formulated as a powder, tablet, capsule, solution, gel tab, dispersion, slurry, suppository, or suspension.

24. The method of claim 1, wherein the sorbent is admixed with food, fluid, or any combination thereof.

25. The method of claim 1, wherein the toxin is one or both of *Clostridium difficile* Toxin A and *Clostridium difficile* Toxin B.

* * * * *